US006755694B2

(12) United States Patent
Ries et al.

(10) Patent No.: US 6,755,694 B2
(45) Date of Patent: Jun. 29, 2004

(54) LEAD UPSIZING SLEEVE

(75) Inventors: Andrew J. Ries, Lino Lakes, MN (US); Jordon D. Honeck, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 10/303,944

(22) Filed: Nov. 25, 2002

(65) Prior Publication Data

US 2003/0073348 A1 Apr. 17, 2003

Related U.S. Application Data

(63) Continuation-in-part of application No. 09/838,814, filed on Apr. 19, 2001, which is a continuation-in-part of application No. 10/040,143, filed on Jan. 3, 2002.

(51) Int. Cl.[7] .......................... H01R 24/04; H01R 27/00
(52) U.S. Cl. ..................... 439/668; 439/669; 439/218
(58) Field of Search ......................... 439/668, 669, 439/218, 46, 48

(56) References Cited

U.S. PATENT DOCUMENTS

| 4,411,277 | A |   | 10/1983 | Dickhundt |
| 4,412,717 | A | * | 11/1983 | Monroe ........................ 439/582 |
| 4,583,543 | A |   | 4/1986 | Peers-Trevarton |
| 4,628,934 | A |   | 12/1986 | Pohndorf et al. |
| 4,934,366 | A | * | 6/1990 | Truex et al. ................... 607/37 |
| 4,934,367 | A | * | 6/1990 | Daglow et al. ............. 439/527 |
| 5,000,177 | A |   | 3/1991 | Hoffmann et al. |
| 5,007,864 | A |   | 4/1991 | Stutz |
| 5,050,602 | A |   | 9/1991 | Osypka |
| 5,060,649 | A |   | 10/1991 | Hocherl et al. |
| 5,076,270 | A |   | 12/1991 | Stutz |
| 5,328,442 | A |   | 7/1994 | Levine |
| 5,374,279 | A |   | 12/1994 | Duffin et al. |
| 5,439,391 | A |   | 8/1995 | McEtchin et al. |
| 5,679,026 | A |   | 10/1997 | Fain et al. |
| 5,697,804 | A |   | 12/1997 | Froberg et al. |
| 5,760,341 | A |   | 6/1998 | Laske et al. |
| 5,766,042 | A | * | 6/1998 | Ries et al. ................... 439/668 |
| 5,843,141 | A |   | 12/1998 | Bischoff et al. |
| 5,975,913 | A | * | 11/1999 | Wada et al. ................... 439/45 |
| 6,044,302 | A |   | 3/2000 | Persuitti et al. |

FOREIGN PATENT DOCUMENTS

| EP | 0 587 379 A2 | 9/1993 |
| WO | WO 00/64535 | 11/2000 |
| WO | WO 02/068050 A1 | 9/2002 |

OTHER PUBLICATIONS

Medtronic Model 5866–45 Sizing Sleeve Technical Manual, Jan. 2002.
Medtronic Model 6925 Sizing Sleeve Kit Technical Manual, Oct. 1996.
Medtronic Model 6920 Sizing Sleeve Kit Manual, Jan. 1997.

* cited by examiner

Primary Examiner—Chandrika Prasad
(74) Attorney, Agent, or Firm—Elisabeth L. Belden; Girma Wolde-Michael

(57) ABSTRACT

A system for coupling a medical electrical lead to a medical device includes an upsizing sleeve having a plurality of spring contacts, a plurality of seal members, and contact members joined in an alternating manner with relatively rigid insulation members. At least one contact member includes an inner surface for housing a contact from the plurality of spring contacts and at least one insulation member includes an inner surface for housing a seal from the plurality of seal members.

34 Claims, 31 Drawing Sheets

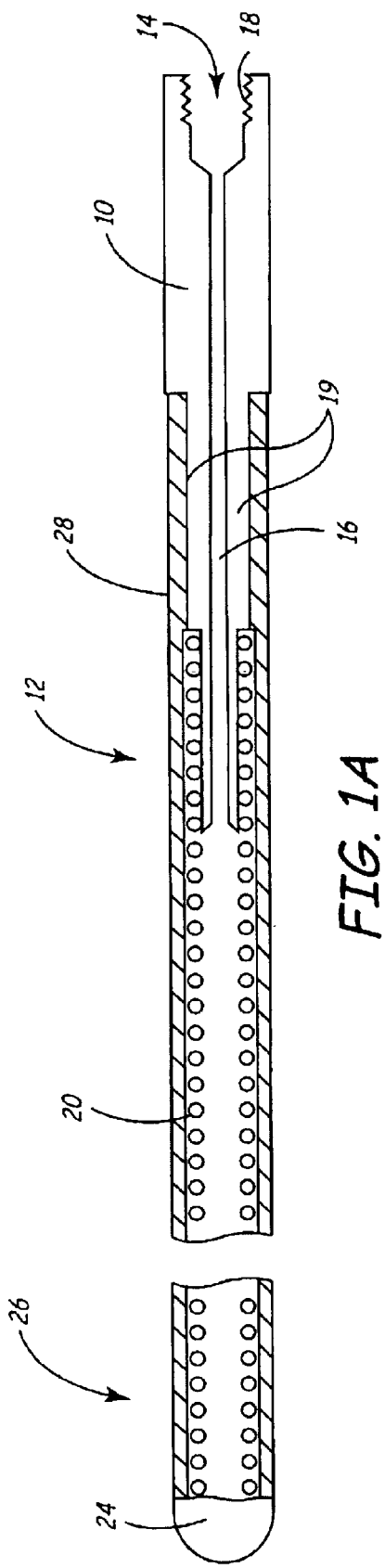
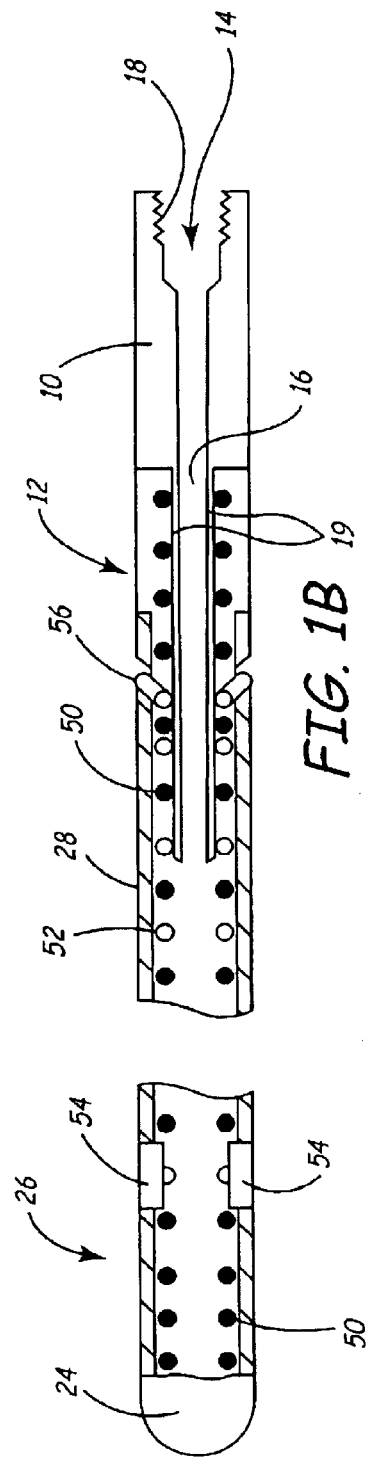
FIG. 1A
FIG. 1B

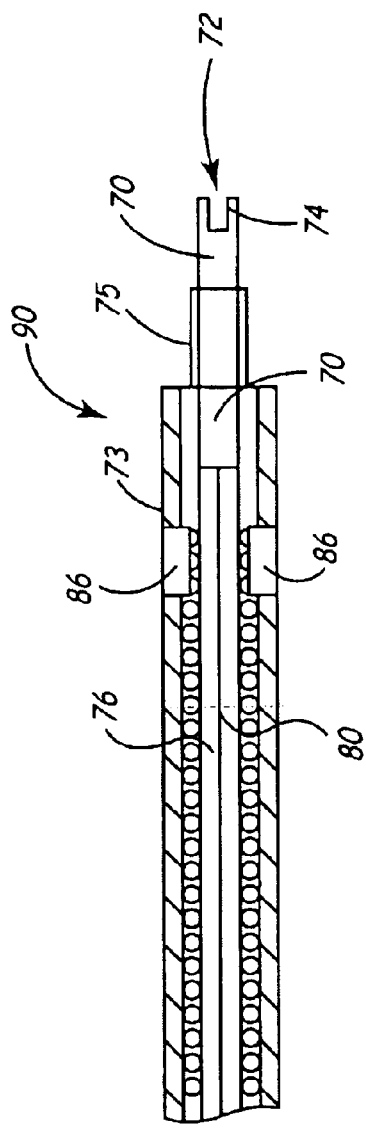
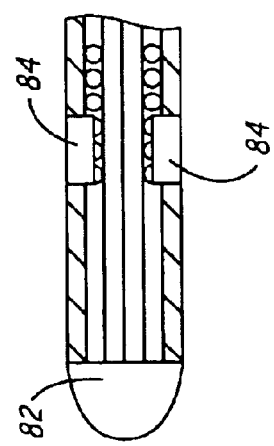
FIG. 1C

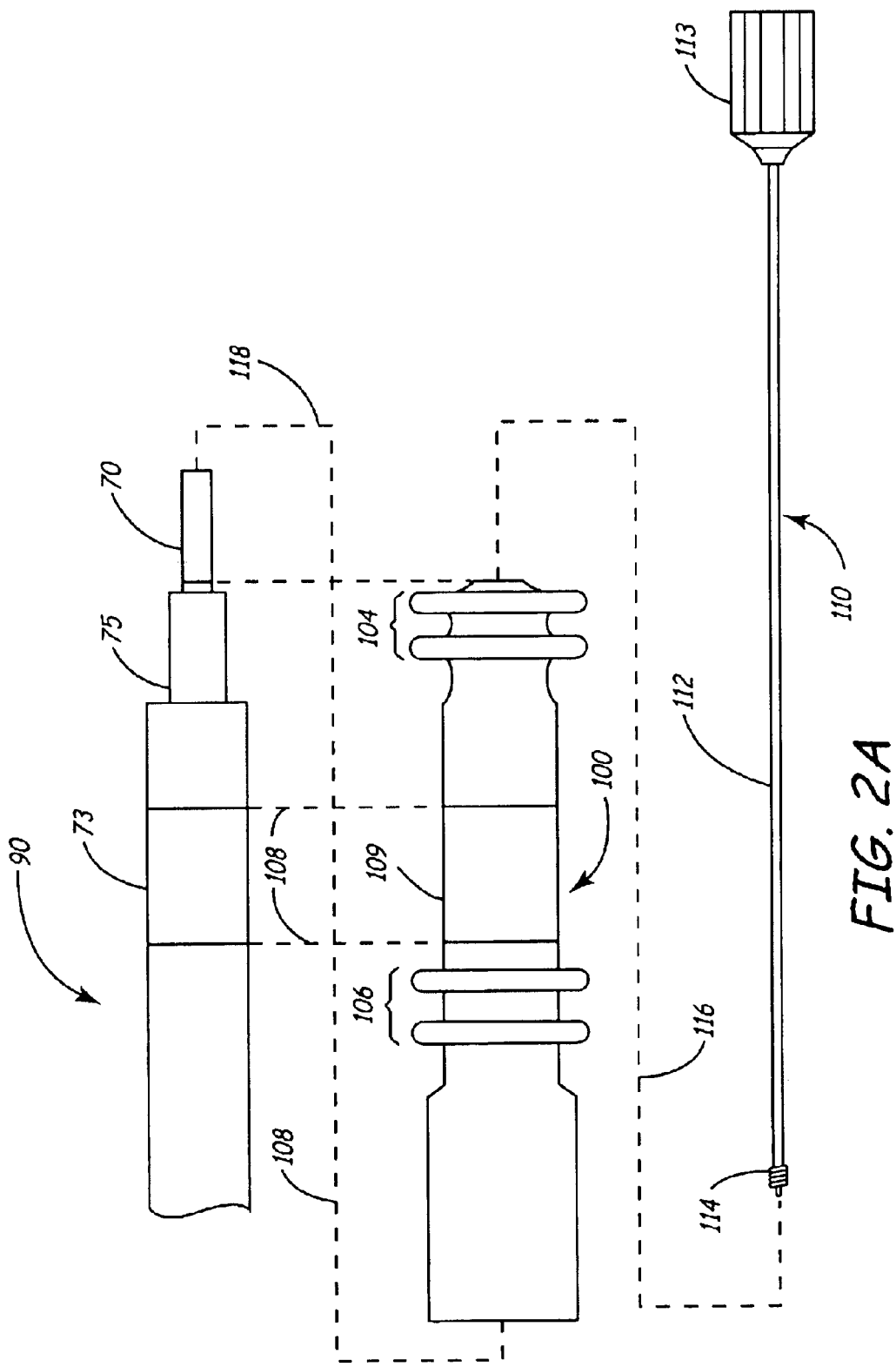

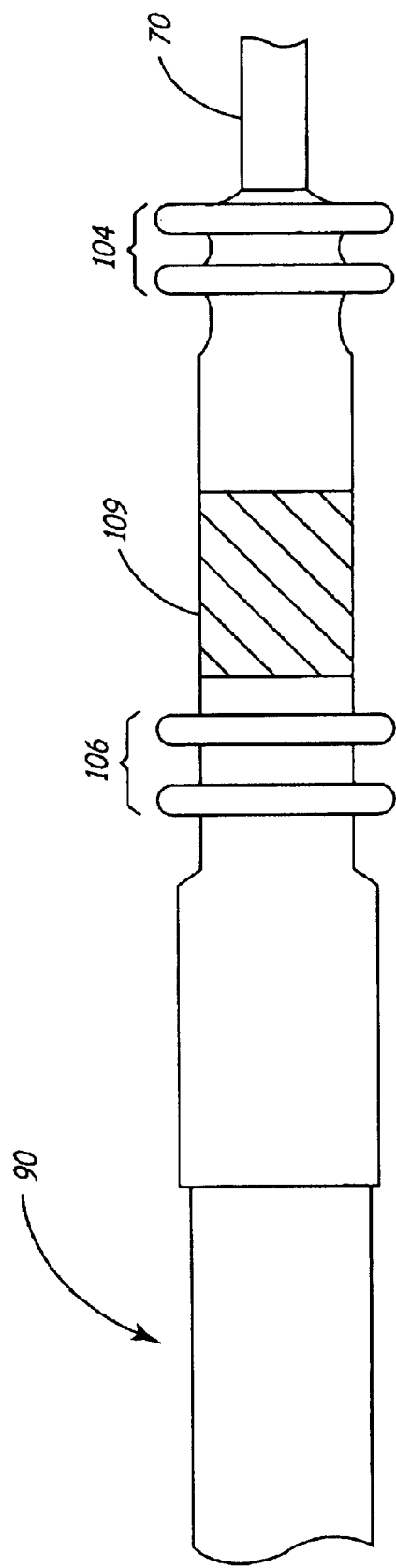

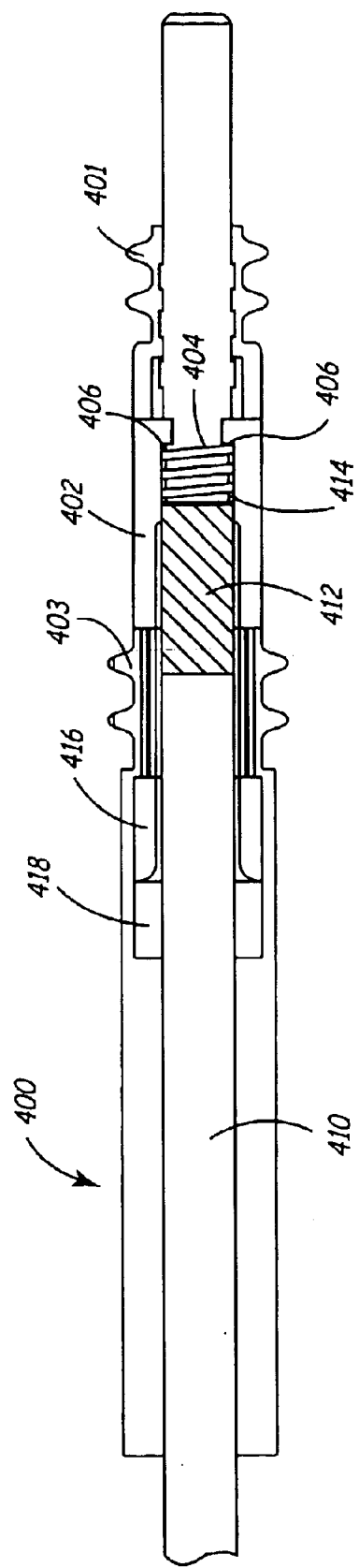

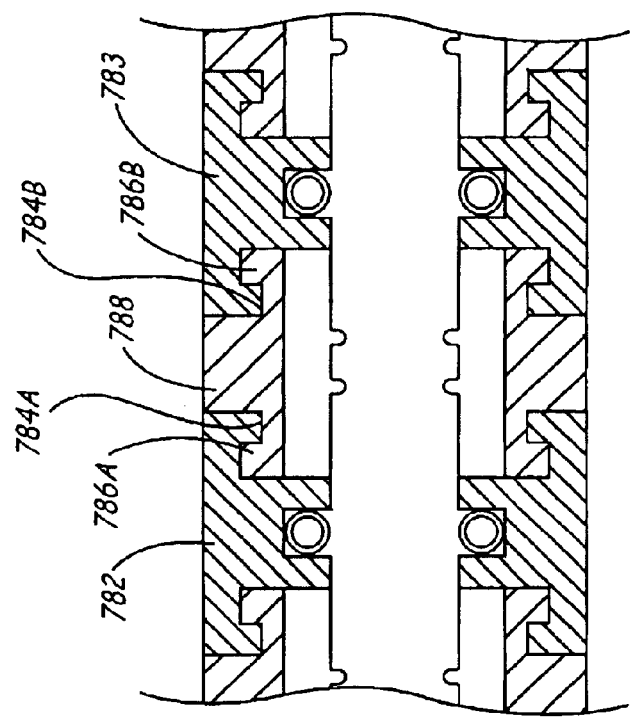
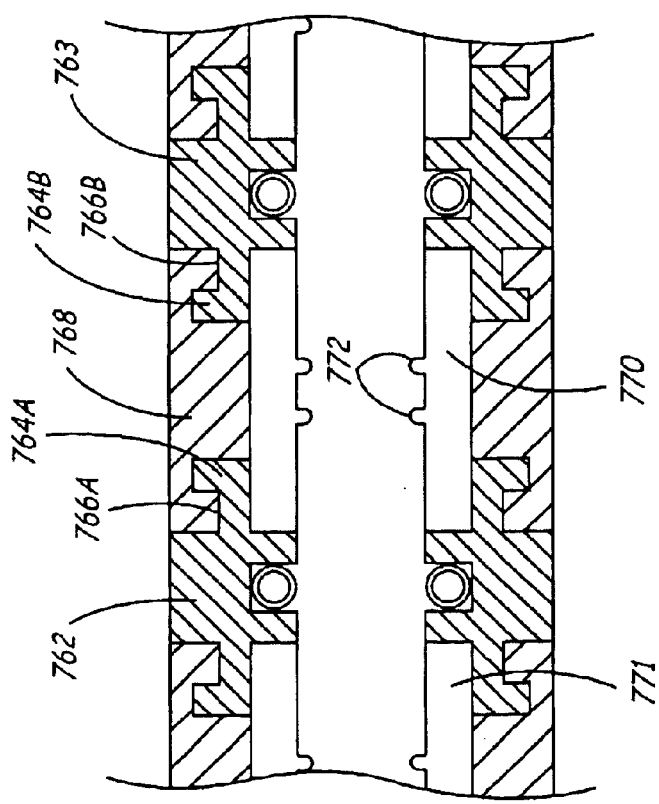

LEAD UPSIZING SLEEVE

PRIORITY CLAIM

This Application is a continuation-in-part of U.S. patent application Ser. No. 09/838,814, filed Apr. 19, 2001, entitled "Lead Up-Sizing Sleeve," which is incorporated herein by reference in its entirety. Cross-reference is made to U.S. patent application Ser. No. 10/040,143, filed Jan. 3, 2002, entitled "Medical Lead and Connector System", which is incorporated herein by reference in its entirety.

FIELD OF THE INVENTION

The present invention relates generally to mechanisms for interconnecting electrical leads and electrical medical devices, and more particularly to systems and methods of interconnecting implantable electrical leads and implantable medical electrical devices such as pacemakers, nerve stimulators, implantable defibrillators, implantable monitors and so forth.

BACKGROUND OF THE INVENTION

Cardiac stimulation systems commonly include a pulse generating device, such as a pacemaker or implantable cardioverter/defibrillator that is electrically connected to the heart by at least one electrical lead. An electrical lead provides an electrical pathway between the pacemaker, connected to the proximal end of the lead, and myocardial tissue, in contact with the distal end of the lead. In such a manner electrical pulses emitted by the pacemaker travel through the lead and stimulate the heart. Intrinsic cardiac signals may be sensed by electrodes located on the lead and conducted via the lead to sense amplifiers in the device for monitoring the heart's natural rhythm.

As implantable electrical devices have increased in their complexity, there have been an increasing variety of electrical lead systems developed for use in conjunction with these devices. Nowhere is this more apparent than in the context of implantable cardioverter/defibrillators, which may include two, three or more leads located for sensing or stimulating up to all four heart chambers. The leads themselves may carry one, two, three, or more electrodes, and may employ a variety of different electrical connector configurations and types. As a result, manufacturers of implantable pacemakers and cardioverter/defibrillators have had to produce their products with a variety of connector block configurations, capable of use with different lead systems. For example, Medtronic, Inc. presently manufactures implantable cardioverter/defibrillators with four basic connector designs, designated configurations "B", "C", "D", and "E". The "B" configuration includes three 6.5 mm connector bores for receiving high voltage electrical lead connectors of the type used to couple to cardioversion/defibrillation electrodes and one IS-1 compatible 3.2 mm in-line electrical connector bore for receiving an IS-1 electrical lead connector of the type generally used to couple to cardiac pacing and sensing electrodes. The "C" configuration includes a single 3.2 mm "DF-1" connector bore for receiving high voltage electrical lead connectors used to couple to cardioversion/defibrillation electrodes and a single IS-1 connector bore. The "D" configuration includes three DF-1 connector bores and one IS-1 connector bore. The "E" configuration includes two 6.5 mm connector bores and two 5 mm connector bores for receiving electrical lead connectors used to couple to individual cardiac pacing and sensing electrodes.

As is apparent from the above discussion, multiple connector block types are necessitated both by the use of multiple connector standards and the desire to connect a varying number of lead systems to a given device. The situation is complicated even further by the use of non-standard connector systems. For example, it has been increasingly common to utilize small-diameter guide catheters to deliver leads having a diameter of 7 French or less to a desired implant site. Down-sized cardiac lead designs have been developed in an effort to make the leads more easily implantable in narrow vessels and to allow multiple leads to be implanted. After lead placement is completed, the catheter must be withdrawn from the patient's body. However, if the catheter has a small inner diameter, the inner lumen of the catheter cannot accommodate a standard-size lead connector such as one conforming portions. Such slittable or splittable catheters are more expensive to manufacture, and require the additional slitting step to remove. To remedy this problem, the lead may instead include a small-diameter, non-standard connector that easily fits within the catheter lumen, allowing the catheter to be readily withdrawn from the body. This non-standard connector has the drawback of necessitating the use of an even larger number of connector block configurations.

Traditionally, incompatibility between the configuration of the connector block and the connector assemblies on the implanted leads has been addressed by means of adapters. Typically, these adapters take the form of a relatively short lead which at one end has a connector assembly which may be inserted into one or more bores on the connector block on the implantable device and at the other end has one or more connector bores capable of receiving the connector assembly or assemblies on the electrical leads to be used with the device. These adapters are bulky and add substantially to the size of the pocket in which the device is to be implanted. In addition, they tend to require a number of additional steps to be performed by the physician in order to couple the leads to the implanted device, and are thus generally seen as undesirable. Such adapters are disclosed in U.S. Pat. No. 5,000,177, issued to Hoffmann, and U.S. Pat. No. 5,328,442, issued to Levine. Some adapters, such as disclosed in U.S. Pat. Nos. 5,050,602 issued to Osypka and 5,060,649 issued to Hocherl et al. even required removal of the connector assembly of the lead as part of the connection process.

Another approach to resolving lead/device incompatibility problems is the upsizing adapter. An upsizing adapter is used to convert a smaller-diameter lead connector to a larger-sized standard connector bore. This is particularly useful when dealing with leads having smaller connectors for use with non-splittable guide catheters. As discussed above, a smaller lead connector allows guide catheters to be easily withdrawn over the lead proximal end after the lead is properly positioned in a desired location. After the guide catheter has been removed from the body, the upsizing adapter may be connected to the proximal lead end to allow the lead to be coupled to a device having a standard connector block.

One example of an upsizing adapter is shown in U.S. Pat. No. 5,007,864, issued to Stutz Jr. This patent discloses an adapter to convert a smaller-diameter unipolar lead system to a larger connector block. Although this system allows a small-diameter lead to be used with a non-splittable catheter, this system has a limitation of not being adaptable for use with bipolar leads.

Another example of an up-sizing adapter is disclosed in U.S. Pat. No. 4,583,543, issued to Peers-Trevarton. While this system is adaptable for use with bipolar lead systems, it can only be used with a lead having a connector pin that is smaller than the connector bore. That is, it is not adaptable for use with a lead having a standard connector pin size but a non-standard connector body size.

What is needed, therefore, is an improved system and method for allowing a lead connector of a first size to couple to a larger-sized device connector, and that addresses the foregoing problems.

BRIEF DESCRIPTION OF THE DRAWINGS

FIG. 1A is a side cutaway view of an exemplary unipolar lead connector of the type that may be employed with the current inventive system.

FIG. 1B is a side cutaway view of an exemplary bipolar lead connector of the type that may be employed with the current inventive system.

FIG. 1C is a side cutaway view of yet another exemplary bipolar lead connector of the type that may be employed with the current inventive system.

FIG. 2A is a plan view of one embodiment of an upsizing sleeve according to the current invention.

FIG. 3 is a plan view illustrating proximal end of the lead of FIG. 1C inserted within upsizing sleeve.

FIG. 10A is a side cutaway view showing an embodiment of the up-sizing sleeve that includes a spring coil to form the electrical connection between a lead ring connector and a conductive ring member of the upsizing sleeve.

FIGS. 22A–B are a side, cut-away views of sections of various additional mating interfaces.

DETAILED DESCRIPTION OF THE INVENTION

Figure 2B:
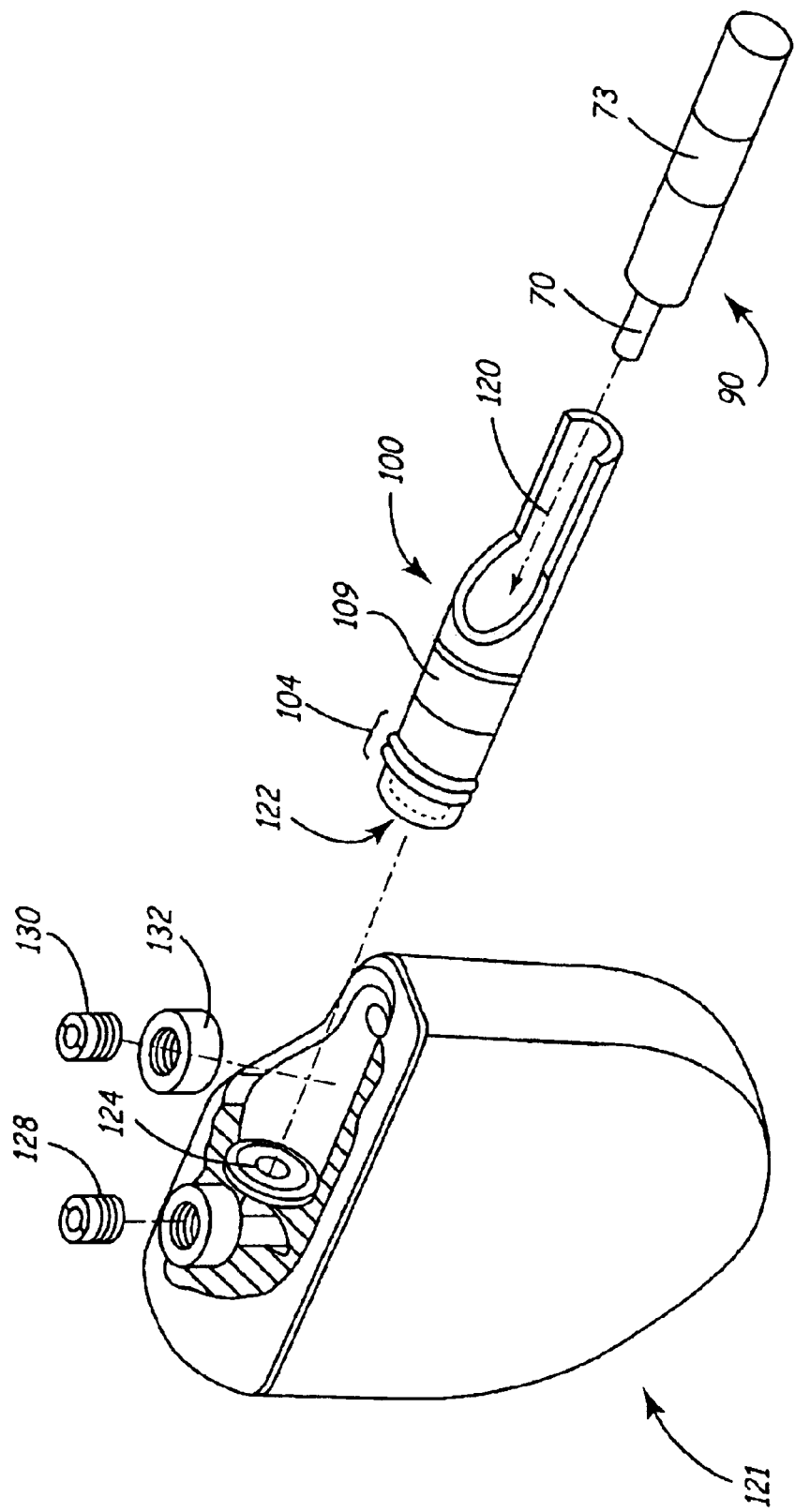
FIG. 2B is a perspective view illustrating the manner in which the inventive up-sizing sleeve may be used to couple a lead to a medical device.

FIG. 1A is a side cutaway view of an exemplary unipolar lead connector of the type that may be employed with the current inventive system. The lead includes a connector pin 10 at the proximal end of the lead. In this view, the connector pin has substantially the same diameter as the lead body 12, although this is not necessary. Connector pin has an opening 14 that extends to inner lumen 16. A portion 18 of inner lumen 16 may be threaded.

Connector pin 10 couples to conductive member 19 that extends into lumen 16 and is electrically and mechanically coupled to at least one conductor 20. In FIG. 1A, conductor 20 is a conductive coil that extends the length of the lead body 12 to a tip electrode 24 at the lead body distal tip 26. In other embodiments, conductor 20 may take the form of a single-filar or multi-filar stranded conductor.

Lead body further includes an insulative jacket 28 that may be formed of a biocompatible polymer such as polyurethane or silicone. It may be noted that the lead of FIG. 1A is merely exemplary, and many other leads may be employed with the current invention. For example, a lead without an inner lumen extending within lead body 12 may be utilized. Alternatively, having multiple inner lumens may likewise be utilized.

FIG. 1B is a side cutaway view of an exemplary bipolar lead connector of the type that may be employed with the current inventive system. In FIG. 1B, elements that are similar to those shown in FIG. 1A are labeled with like designators. The lead of FIG. 1B includes a connector pin 10 that couples to conductive member 19. Conductive member 19 is electrically and mechanically coupled to an insulated coiled conductor 50. This conductor 50 extends the length of lead body 12 and is coupled at the distal tip 26 to tip electrode 24. A second insulated coiled conductor 52 is also provided to couple ring electrode 54 at the lead distal end to ring connector 56. In another embodiment, the conductors may be single or multi-filar stranded conductors.

FIG. 1C is a side cutaway view of yet another exemplary bipolar lead connector of the type that may be employed with the current inventive system. In this embodiment, a connector pin 70 is shown having an opening 72 that includes an inner, threaded surface 74. A portion of the connector pin is shown surrounded by an insulative sleeve 75 which may be formed of a polymer. This insulative sleeve electrically isolates pin from a connector ring 73, and provides additional structural support. The connector pin, which may have dimensions conforming to an IS-1 or another standard, extends within an inner lumen 76 of the lead body 12. This inner lumen houses a stranded conductor 80 such as shown in commonly-assigned U.S. Pat. No. 5,760,341 that is electrically coupled to tip electrode 82. The conductor 80 may be a single or multi-filar stranded conductor, or in a different embodiment, may be a coiled conductor. A second, coiled conductor 84 electrically couples ring electrode 86 to connector ring 73. It may be noted that although the connector pin 70 of this design may be of a dimension that corresponds to a standard such as an IS-1 connector pin standard, the overall lead dimensions of the proximal end 90 of the lead do not necessarily conform to any standard.

As discussed above, the lead configurations shown in FIGS. 1A, 1B, and 1C have small connector profiles. Therefore, a guide catheter used to place the leads during an implant procedure may be readily withdrawn over the connector pin without having to split or slit the catheter body. However, the connector pin 70 and the proximal end 90 of the lead body do not conform to a connector standard such as IS-1, making connection to a standard device connector block difficult. The upsizing sleeve of the current invention is provided as a means for facilitating this connection so that a specialized device connector block is not needed.

FIG. 2A is a plan view of one embodiment of an upsizing sleeve 100 according to the current invention. This upsizing sleeve is a generally tubular member having an inner lumen (not shown in FIG. 2) that is adapted to receive the proximal end of a lead such as the lead shown in FIG. 1C. The inner lumen of the upsizing sleeve is slightly larger than the outer diameter of proximal end 90 of the lead. For example, the proximal end 90 of the lead of FIG. 1C may be adapted to fit within the inner lumen as indicated by dashed line 102 such that the lead body forms a press fit with the surface defined by the lumen. The upsizing sleeve is adapted to conform to a standard configuration such as an IS-1 standard.

Upsizing sleeve is shown to include two sets of exterior sealing rings 104 and 106 adapted to sealingly engage with the connector port of a device such as pacemaker or defibrillator. Upsizing sleeve further includes a conductive ring member 109 adapted to electrically couple to connector ring 73 of the lead, as shown by dashed lines 108 in a manner to be discussed further below. Conductive ring member 109 is further adapted to mechanically and electrically couple to a set screw within the device connector to thereby couple ring connector 73 to a medical device in a manner dictated by the IS-1 connector standard. Sealing rings and the portions of upsizing sleeves surrounding conductive ring member 109 may be formed of one or more polymer structures such as polyurethane or silicone in a manner to be discussed further below.

Because of the relatively tight press-fit between the proximal end 90 of the lead and the upsizing sleeve 100, a pull-wire device 110 may be provided to aid in the insertion process. One embodiment of the pull-wire device 110 includes a rigid pull-wire 112 and a handle 113. The rigid pull-wire 112 may include a threaded distal end 114, which is inserted through the inner lumen of upsizing sleeve 100, as shown by dashed line 116. The threads of threaded distal end 114 are then positioned to engage threaded surface 74 (FIG. 1C) of the connector pin 70, as shown by dashed line 118. This allows the pull-wire 112 to rigidly engage the proximal end 90 of the lead so that the lead may be pulled through the inner lumen of the upsizing sleeve 100.

Although FIG. 2A shows pull-wire 112 including threaded distal end 114 to engage a lead, other coupling means could be provided to coupled to the lead, including a spring-loaded clip, or a plug to form a press-fit with opening 72.

FIG. 2B is a perspective view illustrating the manner in which the inventive up-sizing sleeve may be used to couple a lead to a medical device. The proximal end 90 of a lead such as shown in FIG. 1C includes a connector pin 70 and connector ring 73. This lead may be inserted into the inner lumen 120 of sleeve 100 so that connector ring 73 forms a press fit with conductive ring member 109, with connector pin 70 extending through the proximal end 122 of the sleeve. Connector pin is adapted to be received by port 124 of the medical device 121, which is further maintained by set-screw 128. A second set-screw 130 and washer 132 is provided to form a connection with conductive ring member 109.

FIG. 3 is a plan view illustrating proximal end 90 of the lead of FIG. 1C inserted within upsizing sleeve 100. Connector pin 70 extends through the proximal end of the upsizing sleeve, whereas the lead body of proximal end extends out the distal end of the upsizing sleeve.

Figure 4A:
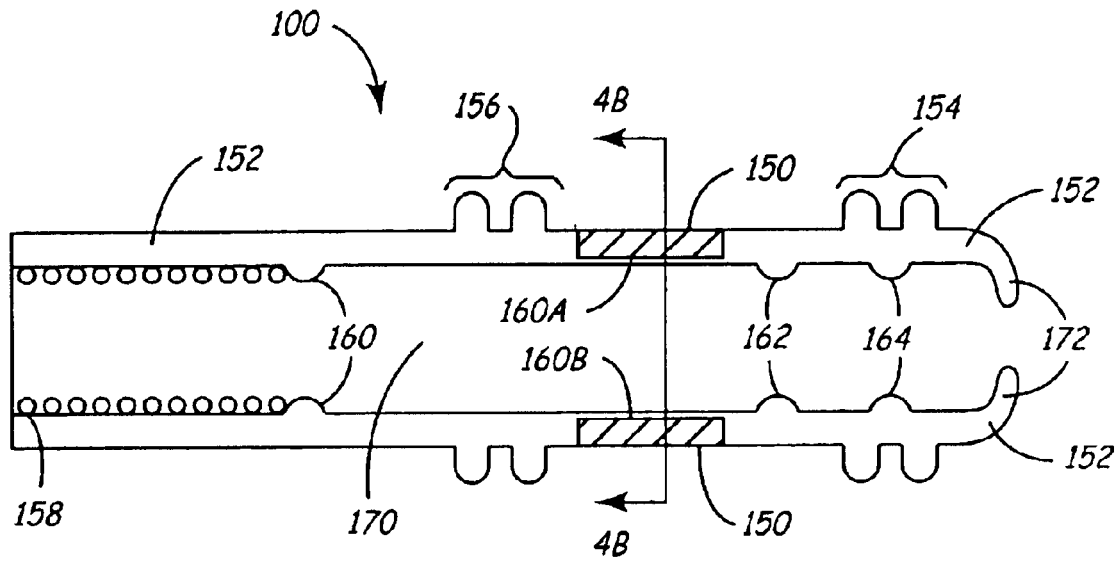
FIG. 4A is a side cutaway view of one embodiment of the upsizing sleeve of the current invention that may be formed using an over-molding process.

FIG. 4A is a side cutaway view of one embodiment of upsizing sleeve 100. A conductive ring member 150 is provided to couple to a connector ring such as connector ring 73 (FIG. 1C) of a lead in the manner discussed above. This ring member may be formed of any conductive material such as a stainless steel, for example. The remainder of the upsizing sleeve is an integral structure 152 that includes sealing rings 154 and 156. This structure may be formed of a biocompatible polymer such as silicone using a silicone over-molding process as is known in the art. According to one aspect of the invention, the upsizing sleeve may be reinforced at the distal end with a reinforcing member 158 that may be formed of an insulative coil such as a PTFE coil, a conductor coil that may or may not be insulated, or any other material having strength properties that make it suitable for this purpose. This reinforcing member provides added support to prevent the lead proximal end 90 (FIG. 3) from flexing in a manner that may cause lead failures over time. In another embodiment, a reinforcing, tubular sleeve member may be inserted within the distal end of the upsizing sleeve to provide this type of support.

Upsizing sleeve may further include interior sealing rings within the inner lumen 170. For example, upsizing sleeve of FIG. 4A includes sealing rings 160, 162 and 164 to provide a fluid-tight seal with a lead inserted within inner lumen 170. Finally, upsizing sleeve is also show to have a lip 172 at the proximal end, which may be provided to engage a corresponding structure on the lead. In this manner, upsizing sleeve is positioned over the lead so that connector pin 70 extends beyond the proximal end of upsizing sleeve 100 a predetermined distance that conforms to a given connector standard. For example, lip 172 may be adapted to engage the ridge formed by insulative sleeve 75 where the insulative sleeve meets the connector 70 (FIG. 1C).

Figure 4B:
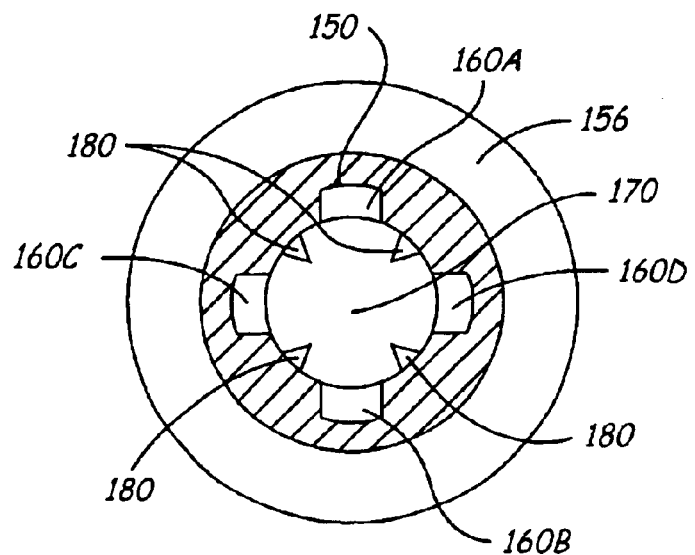
FIG. 4B is a cross-sectional view of upsizing sleeve at line 4B—4B of FIG. 4A.

FIG. 4B is a cross-sectional view of upsizing sleeve at line 4B—4B of FIG. 4A. This view shows conductive ring member 150 including channels adapted to receive a polymer during an over-molding process such as a silicon over-molding process discussed above. The flow of a polymer into these channels results in the formation of the connecting polymer structures 160A, 160B, 160C, and 160D. FIG. 4B further illustrates conductive teeth members 180 coupled to, or integrally formed, in conductive ring member 150. These conductive teeth members are adapted to engage a conductive ring of a lead such as connector ring 73 to form a more robust electrical connection between the connector ring and conductive ring member 150. This view further illustrates sealing rings 156.

Although teeth members 180 are shown in FIG. 4B to couple conductive ring member to a connector ring of a lead, many other mechanisms may be used in the alternative. For example, a keyed mechanism such as a woodruff or spline key may be used to lock a lead ring connector to the conductive ring member. Alternatively, a threaded aperture may be provided in the connective ring member so that a set-screw from a device connector block may be used to affix the sleeve to the lead via the threaded aperture. In yet another embodiment, small ports may be provided in the conductive ring member to receive conductive adhesive to enhance the electrical and mechanical contact between the conductive ring member and the lead ring connector. Alternatively, a hole in the conductive ring member may be aligned with a corresponding hole or groove in the lead so that a pin or rivet can be inserted to form a mechanical and electrical coupling. A thumb-actuated spring and ball-detent mechanism could be used to couple the sleeve to the lead. Another embodiment may include a thumb-activated push-collar such as is provided on steerable stylet handles. Any other type of coupling mechanisms may be used to form a stable electrical and mechanical fit between the conductive ring member and the connector ring of a lead.

Figure 5:
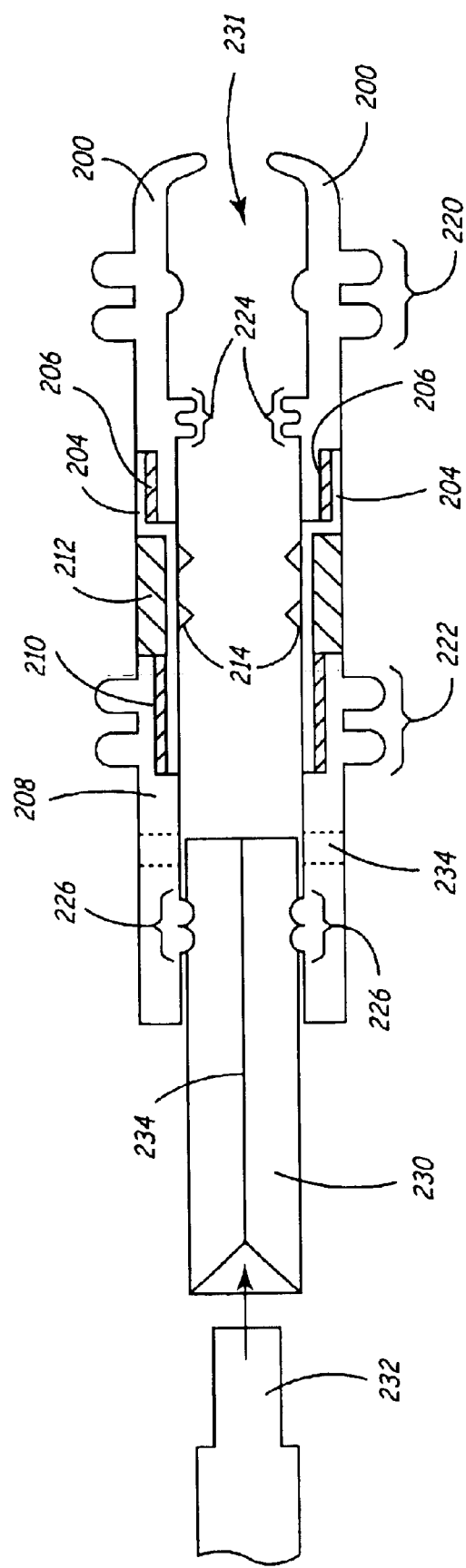
FIG. 5 is a cutaway side view of another embodiment of the upsizing sleeve of the current invention.

FIG. 5 is a cutaway side view of another embodiment of the upsizing sleeve of the current invention. In this embodiment, a first generally tubular member 200 which may be formed of silicone is bonded to a support member 204 using a first layer 206 of medical-grade adhesive. Support member, which may be formed of a material that is more rigid than the silicone such as a higher durometer polyurethane, is also bonded via adhesive layer 210 to a second generally tubular member 208, which may also be silicone. The support member 204 is adapted to provide additional structural rigidity that is not provided by a sleeve formed entirely of a lower-durometer material such as silicone. This rigidity is important to maintain precise sleeve dimensions so that the sleeve maintains a form that conforms to a predetermined standard even after undergoing the strain of forming a press fit with a lead.

A conductive ring member 212 surrounds the support member 204 and is adapted to engage a set-screw of a medical device as is provided on a standard IS-1 device connector block. In one embodiment, the conductive ring member 212 includes teeth 214 that extend through the support member to engage a connector ring of a bipolar lead. If a unipolar lead is to be employed, these teeth need not be included in the sleeve, since the ring connector of the lead need not make an electrical connection with a device connector block.

Each of tubular members 200 and 208 includes exterior sealing rings 220 and 222, respectively, to provide a fluid-tight seal with a device connector block. Each of the tubular members further includes interior sealing rings 224 and 226, respectively, to provide the fluid tight seal with a lead. As discussed above, preferably tubular members 200 and 208 are formed of a less rigid material such as silicone so that these sealing rings are more deformable and better able to provide a seal.

FIG. 5 also illustrates an alternative mechanism that may be used to engage a lead with the sleeve. A split tubular member composed of a material having a lubricious surface such as PTFE tubing 230 may be inserted in the distal end of the sleeve. The lubricious outer surface of the tubing allows the tubing 230 to be readily inserted into inner lumen 231 of the sleeve. A lead 232 may then be inserted within the inner lumen of the tubing 230 and the tubing removed. The slit 234 in the tubing allows it to be removed from around the lead after the lead is attached to the up-sizing sleeve. The use of this split tubular member thereby provides an alternative to the pull-wire tool (FIG. 2) as an aid to forming the press fit between a lead and the sleeve.

In one embodiment, sleeve may include one or more ports such as port 234 (shown dashed) to allow a medical-grade adhesive to be infused or injected between the sleeve and the lead after the lead is inserted into the sleeve to thereby secure the lead to the sleeve.

Figure 6:
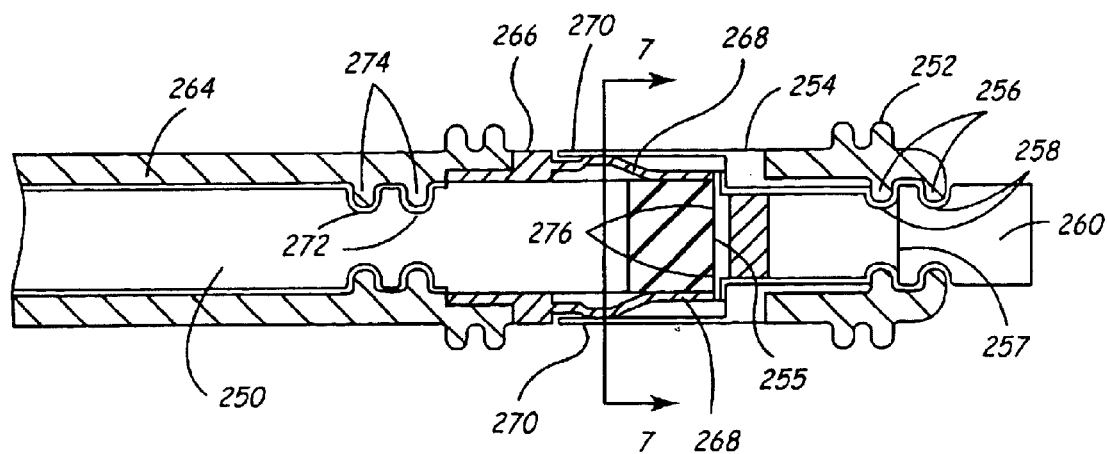
FIG. 6 is a cutaway side view of a two-piece sleeve member that may be assembled over the lead at the time of use.

FIG. 6 is a cutaway side view of a two-piece sleeve member that may be assembled over a lead such as lead 250 at the time of use. A first portion of the sleeve includes a less rigid, generally tubular member 252 that may be formed of silicon, and which is bonded to a conductive ring 254 via a medical-grade adhesive. Conductive ring 254, which is formed of a conductive material, is adapted to electrically and mechanically couple to a connector ring 255 of lead 250 via a second portion of the sleeve, as will be discussed further below. Conductive ring is further adapted to electrically couple to a connector block of a medical device, as may be accomplished using a set-screw.

In one embodiment, the tubular member 252 includes one or more lips 256 to engage grooved members 258 in the lead connector pin 260. This allows the sleeve to be seated over the lead so that the dimensions of the assembly conform to a predetermined standard such as IS-1. Lips 256 further provides a fluid-tight seal with lead 250. One of the lips 256 is shown interfacing with a seal zone 257 of the inline connector. As discussed above, tubular member 252 may be formed of a less rigid material such as silicone to provide sealing rings that allow for a better fluid-tight seal.

The two-piece sleeve of FIG. 6 further includes a second portion that is formed of a second less-rigid tubular member 264 such as silicone. Tubular member 264 is bonded to a connector member 266, which may be formed of a metal. Connector member 266 has deformable fingers 268 that slide under edge 270 to engage conductive ring 254 in a snap-fit that provides both a mechanical and electrical coupling between connector member 266 and conductive ring 254. Deformable fingers 268 also electrically couple to connector ring 255 of lead 250 so that an electrical connection is formed between the connector ring 255 and conductive ring 254 of the two-piece sleeve. This allows the connector ring 255 of lead 250 to be coupled to a connector block of a device via conductive ring 254.

The lead 250 of FIG. 6 may include grooves 272 to engage inner sealing rings 274, and may further having a shoulder 276 to engage conductive ring 254 in a manner that further allows the lead to seat in a position that conforms to a predetermined standard.

Figure 7:
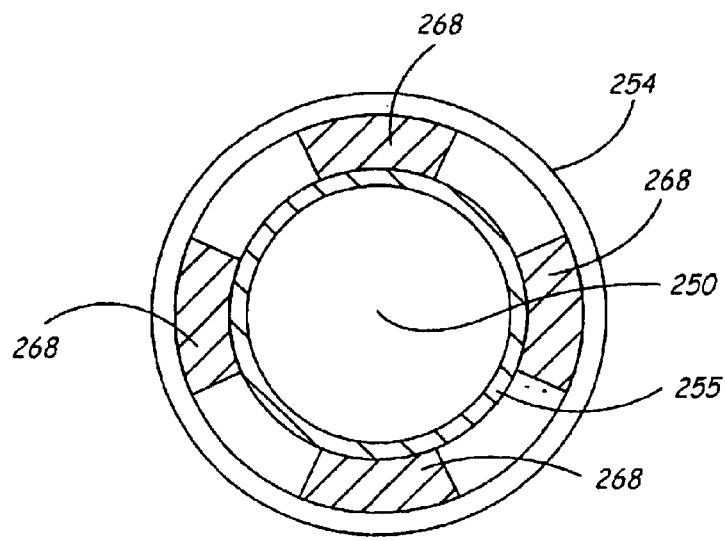
FIG. 7 is a cross-sectional view of the sleeve of FIG. 6 at line 7—7.

FIG. 7 is a cross-sectional view of the sleeve of FIG. 6 at line 7—7. This view shows the deformable fingers 268 electrically and mechanically engaging conductive ring 254, and further electrically engaging connector ring 255 of lead 250.

Figure 8:
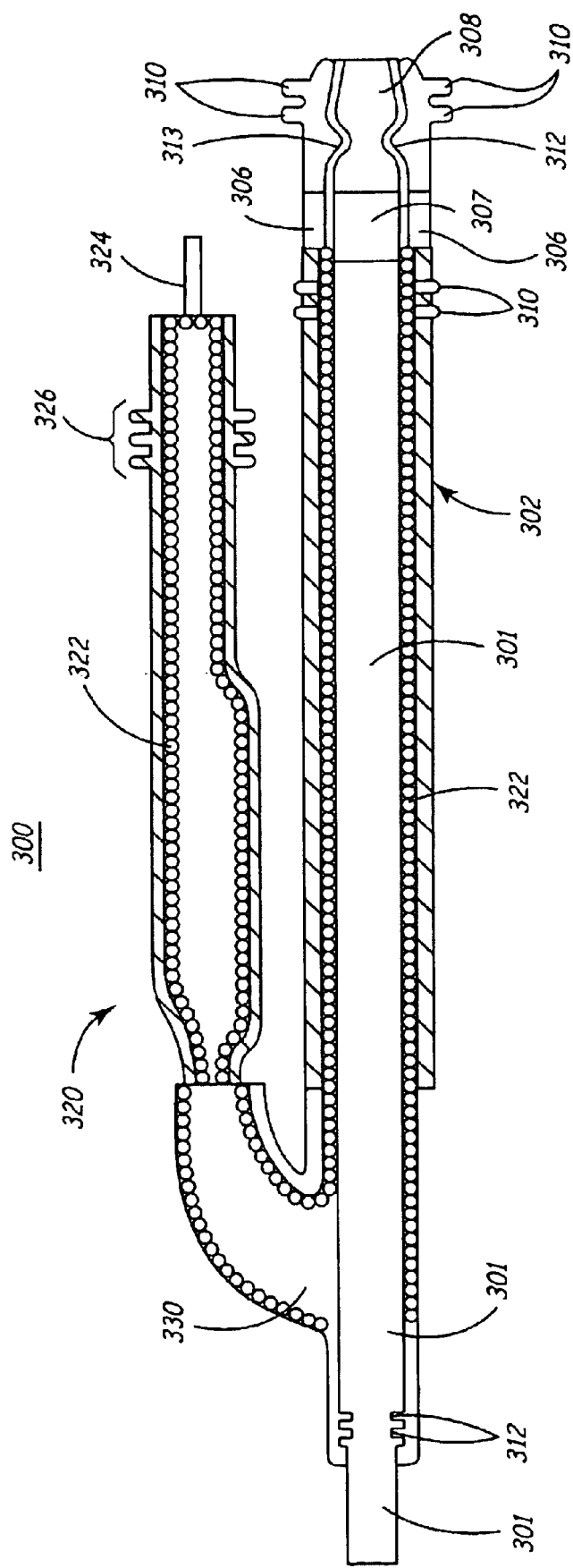
FIG. 8 is a cutaway side view of a bifurcated sleeve that includes two different connector standards.

FIG. 8 is a cutaway side view of a bifurcated sleeve 300 designed to adapt a lead to conform to two different connector standards. In the embodiment illustrated, lead 301 is shown engaging a first bifurcation leg 302 of the bifurcated sleeve that conforms to the IS-1 standard. This portion of the sleeve may be of any of the embodiments discussed above. A conductive ring member 306 is provided on bifurcation 302 to engage with a connector ring 307 of lead 301, and to further engage a connector block of a medical device in the manner discussed above. The pin 308 of the lead extends through the sleeve as discussed above, and exterior sealing rings 310 provide a fluid-tight fit with the medical device. Interior sealing rings 312 and 313 provide a fluid-tight fit with lead 301. Additional inner sealing rings (not shown) are provided to engage the proximal end of the lead as discussed above.

In this embodiment, pacing and sensing of a patient may be accomplished via ring connector 306 and pin 308 connectors, which coupled to tip and ring electrodes (not shown in FIG. 8), respectively, at the lead tip. Further assume the lead carries a high-voltage coil electrode that is electrically coupled to ring connector 306. An offset bifurcation leg 320 may then be used to provide a connector for cardioversion/defibrillation purposes. A high-voltage defibrillation coil 322 connects conductive ring member 306 with a connector pin 324 that may conform to a second standard such as a DF-1 standard. This connector pin 324 may be utilized by a medical device to deliver a cardioversion/defibrillation shock that is then carried via coil 322 and conductive ring member 306 to conductor ring 307, and finally to the defibrillation coil electrode as the proximal end of the lead. This embodiment of the sleeve thereby allows a bipolar lead having a pace/sense electrode pair and a single shock coil to be adapted to both IS-1 and DF-1 connector blocks without the need to slit or split a catheter that is used during lead delivery. Additionally, the current inventive sleeve eliminates the pocket bulk associated with traditional longitudinal adaptors.

Sleeve 300 may be formed of one or more biocompatible polymers. For example, the hub portion 330 of the bifurcated sleeve could be formed of a more rigid material such as polyurethane that provides additional support to the structure and to the proximal end of the lead. The remainder of the sleeve, including the portions of the legs 302 and 320 that include the exterior sealing rings 310 and 326, could be formed of a less rigid material such as silicone.

As noted above, the current inventive up-sizing sleeve is, in its preferred embodiment, designed to conform a lead to a predetermined connector standard. For this reason, it is important that the sleeve does not stretch or deform in any manner. To provide a structure that maintains precise dimensions, more rigid support structures formed of a material such as polyurethane may be incorporated into the sleeve. The inclusion of additional sealing grommets may also be desirable to ensure both a fluid-tight seal, and the retention of predetermined sleeve dimensions.

Figure 9:
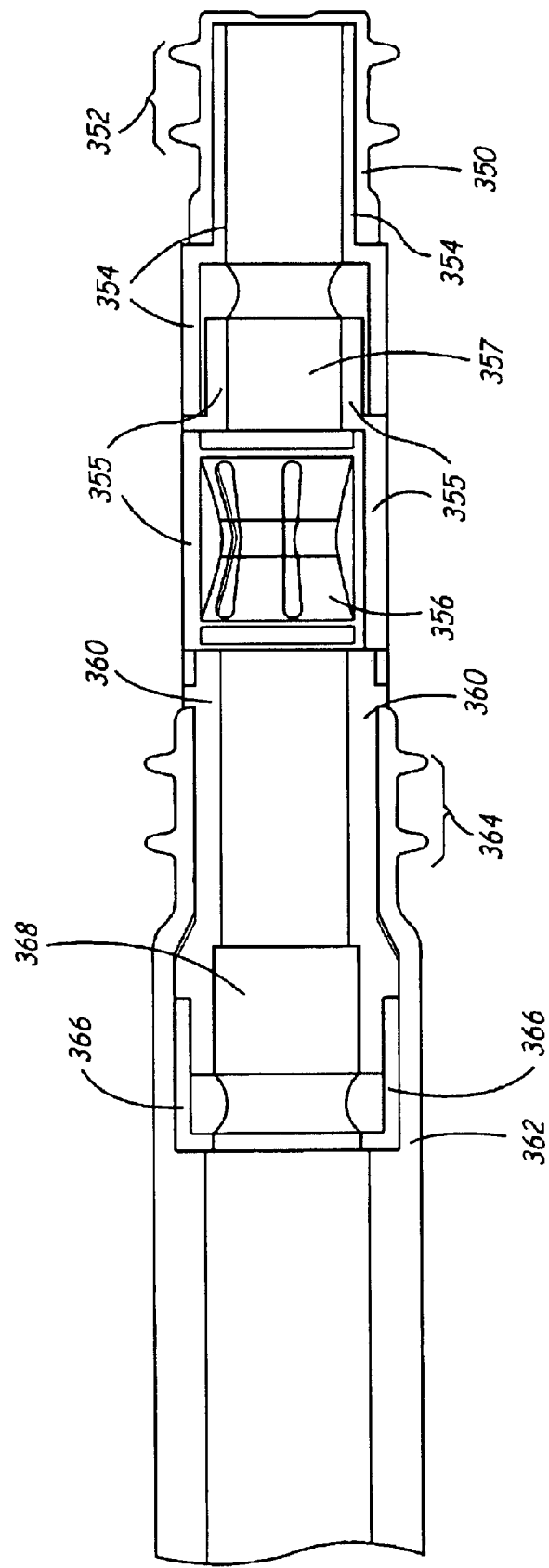
FIG. 9 is a side cutaway view of another embodiment of the current invention that incorporates both support structures and sealing grommets.

FIG. 9 is a side cutaway view of another embodiment of the current inventive up-sizing sleeve that incorporates both support structures and sealing grommets. A first, less-rigid tubular sleeve member 350 is shown having exterior sealing rings 352 as discussed above. Tubular member 350, which may be formed of a silicone, is bonded to a more rigid tubular support member 354, which may be formed of a polyurethane. Support member 354, is, in turn, coupled at one end to an exterior conductive ring 355 formed of an electrically-conductive material that is adapted to make an electrical connection with a connector block of a medical device, as is provided by a standard IS-1 connector.

Conductive ring 355 houses, and is mechanically and electrically coupled to, a connector member 356 that is also formed of a conductive material. Connector member 356 is adapted to make an electrical and mechanical connection with a connector ring of a lead in a manner similar to that discussed above. Connector member 356 is shown in this embodiment to be a multi-beam connector having deformable fingers adapted to form a press-fit with a lead connector ring. Alternatively, connector member 356 may take the form of any other type of connector known in the art, including any of the types of connectors discussed above.

Housed within conductive ring 354 may be a sealing grommet 357 provided to form a superior fluid-tight seal with a lead. Sealing grommet 357 may be formed of a more deformable material such a silicone, for example.

Conductive ring 355 is further bonded or welded to a second rigid tubular support member 360, which may be formed of a polyurethane or a metal. This second tubular support member 360 is also mechanically coupled to a less rigid, tubular sleeve member 362 having sealing rings 364, and which may be formed of silicone. Tubular support member 360 is bonded to a lip member 366 adapted to house a second sealing grommet 368. Lip member 366 may be formed of a rigid polymer such as a polyurethane, whereas the sealing grommet may be formed of silicone.

The embodiment shown in FIG. 9 provides a more flexible design. The length of the sealing grommets may be adjusted to position the conductive ring 355 based on a selected connector standard. Moreover, the multi-beam connector shown as connector member 356 may be adjusted to couple to any lead size requirement. This design is adaptable for over-the-wire leads, and small coil-over-cable leads having an outer diameter of 5 French or less.

It may be noted that while the multi-beam connector 356 of FIG. 9 may be adapted to form an electrical connection with a connector ring of a multi-polar lead, this need not be the case. In one embodiment, the multi-beam connector 356 may be formed of a non-conductive material. In this case, the connector 356 is adapted to form a mechanical connection with a unipolar lead so that the lead body is maintained in a stable position with respect to the up-sizing sleeve. In this embodiment, conductive ring 355 may be omitted if desired, or a similar structure may be provided that is formed of a non-conductive material.

FIG. 10A is a side cutaway view showing yet another embodiment of the up-sizing sleeve that includes a spring coil to form the electrical connection between a lead ring connector and a conductive ring member of the upsizing sleeve 400. Up-sizing sleeve 400 includes many of the components described above with respect to other ones of the embodiments of the invention. For example, the embodiment of FIG. 10A includes flexible tubular members 401 and 403 which may be formed of a silicone, and which are coupled as with a medical-grade adhesive to an electrically-conductive ring member 402. Most notably, in this embodiment, conductive ring member 402 is electrically and mechanically coupled at one end to a deformable spring coil 404. Spring coil 404, which is formed of an electrically-conductive material, may be spot welded or otherwise coupled to a shoulder 406 of conductive ring member 402. In this embodiment, lead 410 includes a ring conductor 412 having a lip 414 to engage spring coil 404. In this manner, ring connector 412 is electrically coupled to the conductive ring member 402, which, in turn, may be coupled to the connector block of a medical device. The upsizing sleeve may further include one or more grommets such as grommet 416, which is maintained in position by a polyurethane lip member 418 similar to that shown in the embodiment of FIG. 9. The upsizing sleeve may further include other aspects described with respect to the embodiments of FIGS. 1–9 as would be apparent to those skilled in the art.

Figure 10B:
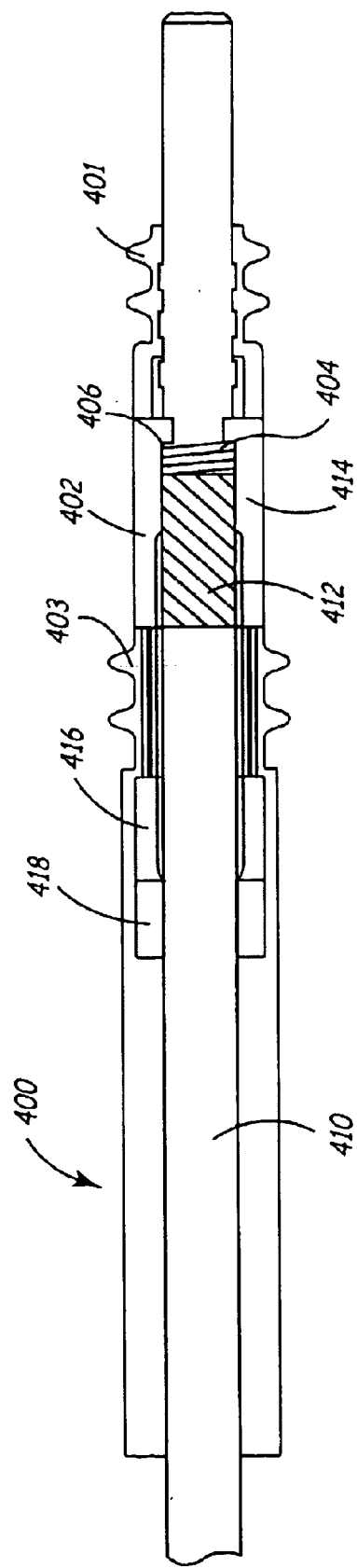
FIG. 10B is a side cutaway view of the embodiment of FIG. 10A illustrating the manner in which the spring coil compresses when the lead is fully inserted within the up-sizing sleeve.

FIG. 10B is a side cutaway view of the embodiment of FIG. 10A illustrating the manner in which the spring coil 404 compresses when the lead is fully inserted within the up-sizing sleeve 400.

Figure 11A:
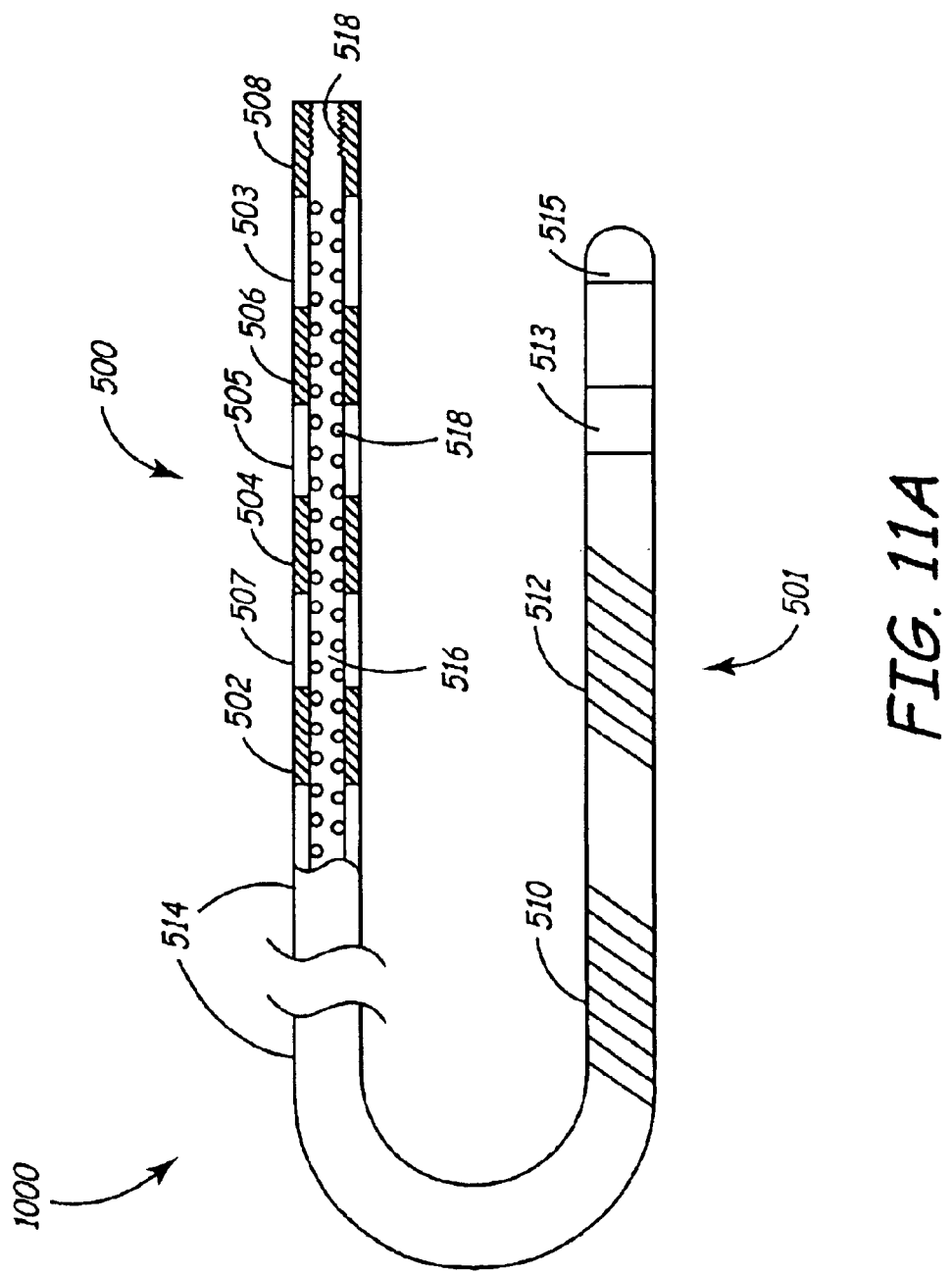
FIG. 11A is a partially cutaway plan view of a quadripolar lead of the type that may be employed with an alternative embodiment of the current inventive system for use in connecting a multi-polar lead to a medical device.

In FIG. 11A, a lead 1000 includes a lead body 514 and connector rings 502, 504, 506, and 508 disposed about a proximal end 500. Connector rings 502, 504, 506, and 508 are electrically isolated from each other by insulative spacers 503, 505 and 507. As illustrated in FIG. 11, a multi-filar coiled conductor 518, having a lumen 516, extends over a length of lead 1000 and each filar included in coiled conductor 518 is electrically coupled to one of connector rings 502, 504, 506 and 508. Each filar is further coupled to a corresponding electrode located at or near a distal end 501 of lead 1000.

The exemplary lead shown in FIG. 11A is a quadripolar lead having a tip electrode 515, a ring electrode 513, and two defibrillation coil electrodes 510 and 512. Other multipolar leads that may be used with the current inventive system may include any combination of a tip electrode, and/or ring electrodes and/or defibrillation coil electrodes or other types of sensors. In other exemplary lead embodiments, the lead body 514 may also be provided as a multi-lumen lead body for carrying multiple conductors, which may be cabled, stranded or coiled conductors. Each conductor provides electrical coupling between one of two, three, four, or more electrodes at a distal lead end and a corresponding connector ring at a proximal lead end.

As illustrated in FIG. 11A, a threaded surface 518 is included within an inner diameter of the connector ring 508. As will be further described below, threaded surface 518 may be used to engage a pull tool used for inserting proximal lead end 500 into an upsizing sleeve according to the current invention.

Figure 11B:
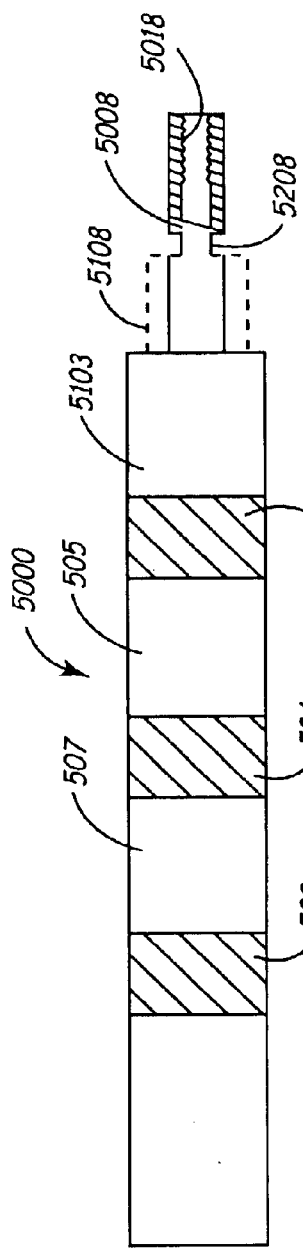
FIG. 11B is a partially cutaway plan view of an alternate embodiment of a proximal end of the quadripolar lead of FIG. 11A.
Figure 11C:
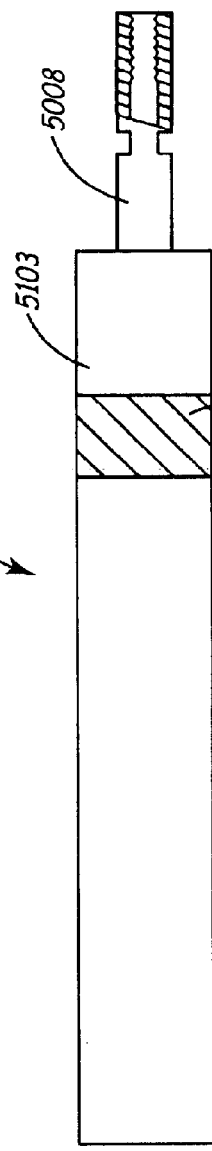
FIGS. 11C–D are partially cutaway plan views of alternate embodiments of a proximal end of the quadripolar lead of FIG. 11A
Figure 11D:
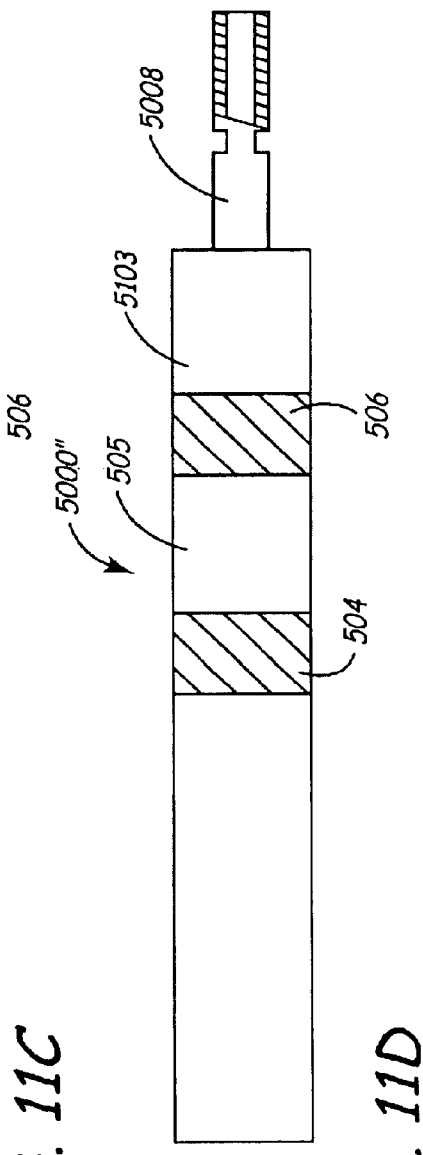

FIG. 11B is a partially cutaway plan view of an alternate embodiment of a proximal end of the quadripolar lead of FIG. 11A. As illustrated in FIG. 11B a proximal end 5000 includes a connector pin 5008. Connector pin 5008 may be of a single diameter or may have a distal portion 5108, illustrated with dashed lines, that has an increased diameter. As illustrated in FIG. 11B, connector pin 5008 includes a threaded surface 5018, within an inner diameter, and a retention groove 5208. As will be further described below, threaded surface 5018 may be used to engage a pull tool used for inserting the proximal lead end 5000 into an upsizing sleeve and retention groove 5208 may engage a retention member in a connector port. Connector rings 502, 504, and 506 are electrically isolated from each other by insulative spacers 505 and 507, and connector ring 506 is isolated from connector pin 5008 by a most proximal insulative spacer 5103. FIGS. 11C–D are partially cutaway plan views of alternate embodiments of a proximal end of the quadripolar lead of FIG. 11A. A bipolar proximal end 5000' is shown in FIG. 11C having only connector ring 506 and insulative spacer 5103. A tri-polar proximal end 5000" is shown in FIG. 11D having connector rings 504 and 506 and insulative spacers 505 and 5103. It should be noted that the embodiment of FIG. 11A may also have alternate embodiments in a bipolar and tri-polar form and further embodiments of proximal ends of leads may include greater numbers of connector rings and spacers than have been illustrated herein. Additionally, proximal ends 5000' and 5000" of embodiments depicted in FIGS. 11C–D, may be isodiametric.

Figure 12A:
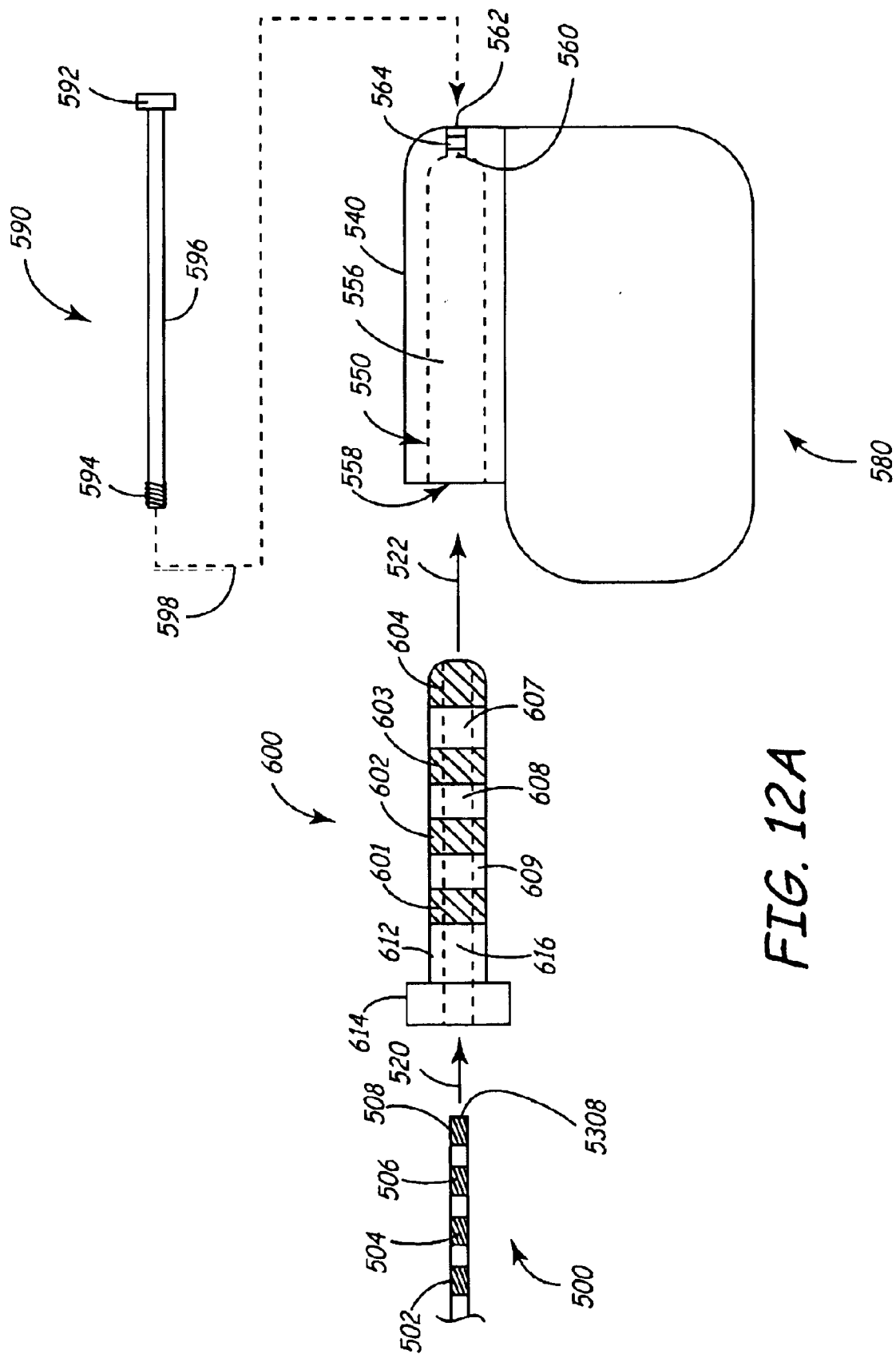
FIG. 12A is a plan view of one embodiment of an upsizing sleeve.

FIG. 12A is a plan view of one embodiment of an upsizing sleeve 600 and further illustrates the manner in which upsizing sleeve 600 may be used for coupling proximal end 500 of a multi-polar lead to a medical device 580. Upsizing sleeve 600, a generally tubular member having an inner lumen 616, as indicated by dashed lines, is adapted to receive proximal end 500 of a lead, such as the lead shown in FIG. 11A.

As illustrated in FIG. 12A, upsizing sleeve 600, having a lumen 616, includes conductive ring members 601, 602, 603 and 604, separated by relatively rigid insulation members 607, 608, and 609, and a distal portion 612 including a knob 614. Conductive ring members 601, 602, 603 and 604 enable electrical connection with one or more of connector rings 502, 504, 506, 508. When proximal end 500 is fully inserted into lumen 616 of upsizing sleeve 600, contact members 601, 602, 603 and 604 will be aligned with connector rings 502, 504, 506, and 508, respectively. Relatively rigid insulation members 607, 608, and 609, along with distal portion 612 provide means for a fluid tight seal about proximal end 500 within lumen 616. Conductive ring members 601, 602, 603 and 604, insulation members 607, 608, and 609, and distal portion 612 together form a portion of an external surface of upsizing sleeve 600 which conforms to predetermined dimensions corresponding with a connector block port 550, indicated by dashed lines, which may be an industry standard connector block port. An outer diameter of the external surface of upsizing sleeve 600 may be between approximately 3 mm and approximately 3.5 mm. As illustrated in FIG. 12A, a medical device 580, which may be a pacemaker, defibrillator, or other type of implantable stimulator or sensing device, includes a connector block 540; connector block 540 includes port 550 having a lumen 556 continuous with a smaller diameter lumen 560, which extends through the connector block 540 such that port 550 has a proximal opening 558 and a distal opening 562.

In one method for using upsizing sleeve 600 to couple proximal lead end 500 to connector port 550, upsizing sleeve 600 may first be fully inserted into connector port 550 through proximal opening 558 as indicated by an arrow 522. Knob 614 may be employed to facilitate insertion by providing an enlarged area where sleeve 600 may be grasped. Next, a pull tool 590 may be inserted through distal opening 562, as indicated by a dashed arrow 598, and advanced through lumen 560 and inner lumen 616 of upsizing sleeve 600 until it exits proximal opening 558. The pull tool 590 is then inserted into lead proximal end 500 in order to engage with threaded surface 518 (shown in FIG. 11).

Pull tool 590 is provided with a handle 592, a shaft 596 and a threaded distal end 594. Threaded distal end 594 is provided to engage with the threaded surface 518 of lead proximal end 500. In other embodiments, distal end 594 may engage proximal end 500 by a press fit, a spring mechanism, or other engagement mechanism. Once engaged, the pull tool may be withdrawn back through lumen 616 until proximal end 500 is completely inserted into upsizing sleeve 600 such that connector rings 502, 504, 506, and 508 are properly aligned with corresponding contact members 601, 602, 603, and 604 of upsizing sleeve 600.

Pull tool 590 may then be disengaged from proximal end 500 and removed through lumen 560. A grommet 564 may be provided just inside opening 562 in order to seal lumen 560 from bodily fluids after pull tool 590 has been removed.

In another method for using upsizing sleeve 600, lead proximal end 500 may first be inserted into upsizing sleeve 600 as indicated by arrow 520. This insertion step may be aided by the use of pull tool 590. Next, upsizing sleeve 600, with proximal end 500 already fully inserted therein, may be inserted into connector port 550 by applying force to knob 614.

Pull tool 590 and method for use with a connector block and lead connector assembly may correspond generally to that disclosed in U.S. Pat. No. 5,843,141 issued to Bischoff, et al., incorporated herein by reference in its entirety. The methods of some embodiments of the present invention provide for the use of an upsizing sleeve in conjunction with a pull tool, lead connector assembly, and connector block, as illustrated in FIG. 12A, however, other embodiments of the present invention are not limited in scope to features supporting such methods. For example, upsizing sleeve 600 could be pushed into port 550 and lead proximal end 500 could be pushed into lumen 616 of upsizing sleeve 600 without need for pull tool 590.

Figure 12B:
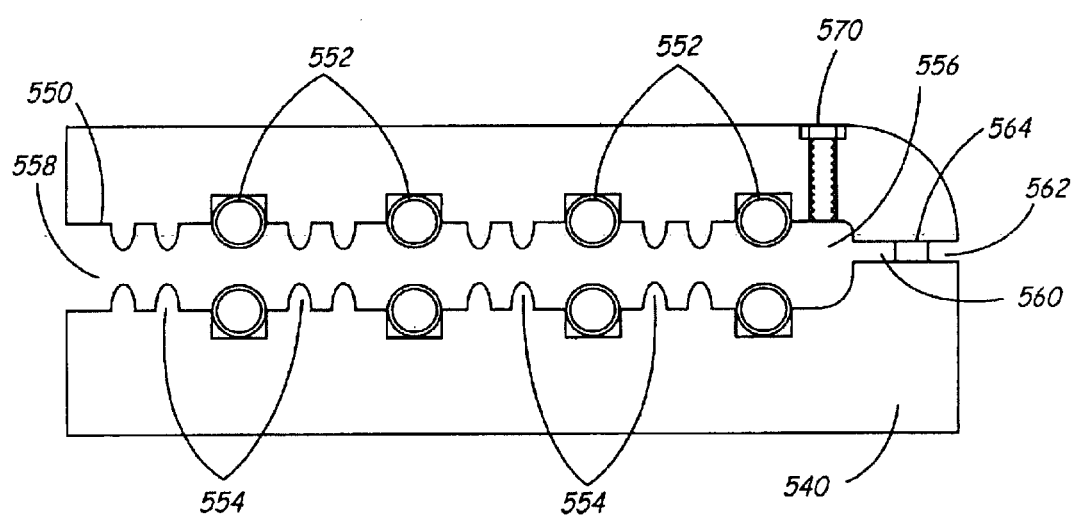
FIG. 12B is a side cut-away view of the connector block port of FIG. 12A.

FIG. 12B is a side cut-away view of connector block port 550. Port 550 is an exemplary port of the type that may be used in conjunction with the upsizing sleeve 600. Port 550 provides a lumen 556 for receiving upsizing sleeve 600 through opening 558. As illustrated in FIG. 12B, port 550 includes multiple electrical contacts 552 alternating with inner sealing rings 554. Electrical contacts 552 are aligned with contact members 601, 602, 603, and 604 and inner sealing rings 554 provide a fluid tight seal with upsizing sleeve 600 by interfacing with insulation members 607, 608, 609 and 612, when upsizing sleeve 600 is fully inserted into port 550, as illustrated in FIG. 13.

Figure 12C:
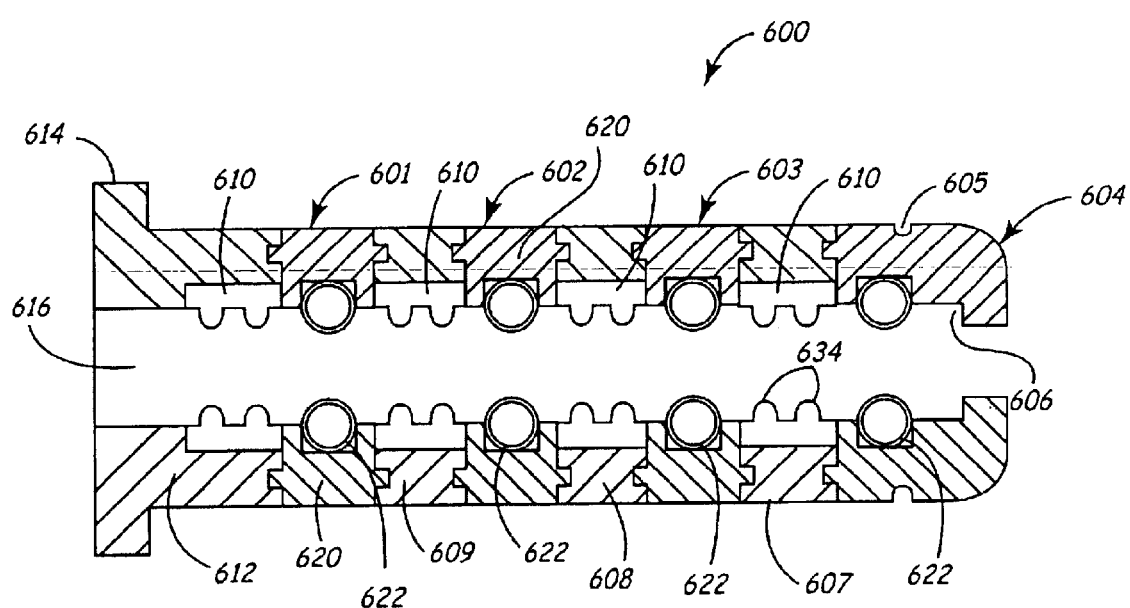
FIG. 12C is a side cut-away view of the upsizing sleeve of FIG. 12A.

FIG. 12C is a side cut-away view of upsizing sleeve 600. The inner lumen 616 for receiving proximal lead end 500 is generally formed by electrical contact members 601, 602, 603, and 604 alternating with insulation members 607, 608, 609, and distal portion 612. As illustrated in FIG. 12C, a seal member 610 resides within an inner surface of each insulating member 607, 608, 609, and distal portion 612, and a coil spring contact 622 resides within an inner surface of each contact member 601, 602, 603, 604. Seal members 610 engage lead proximal portion 500, as illustrated in FIG. 13, to ensure electrical isolation between an electrical coupling of each of the contact members 601, 602, 603 and 604 with each of the connector rings 502, 504, 506 and 508.

Figure 13:
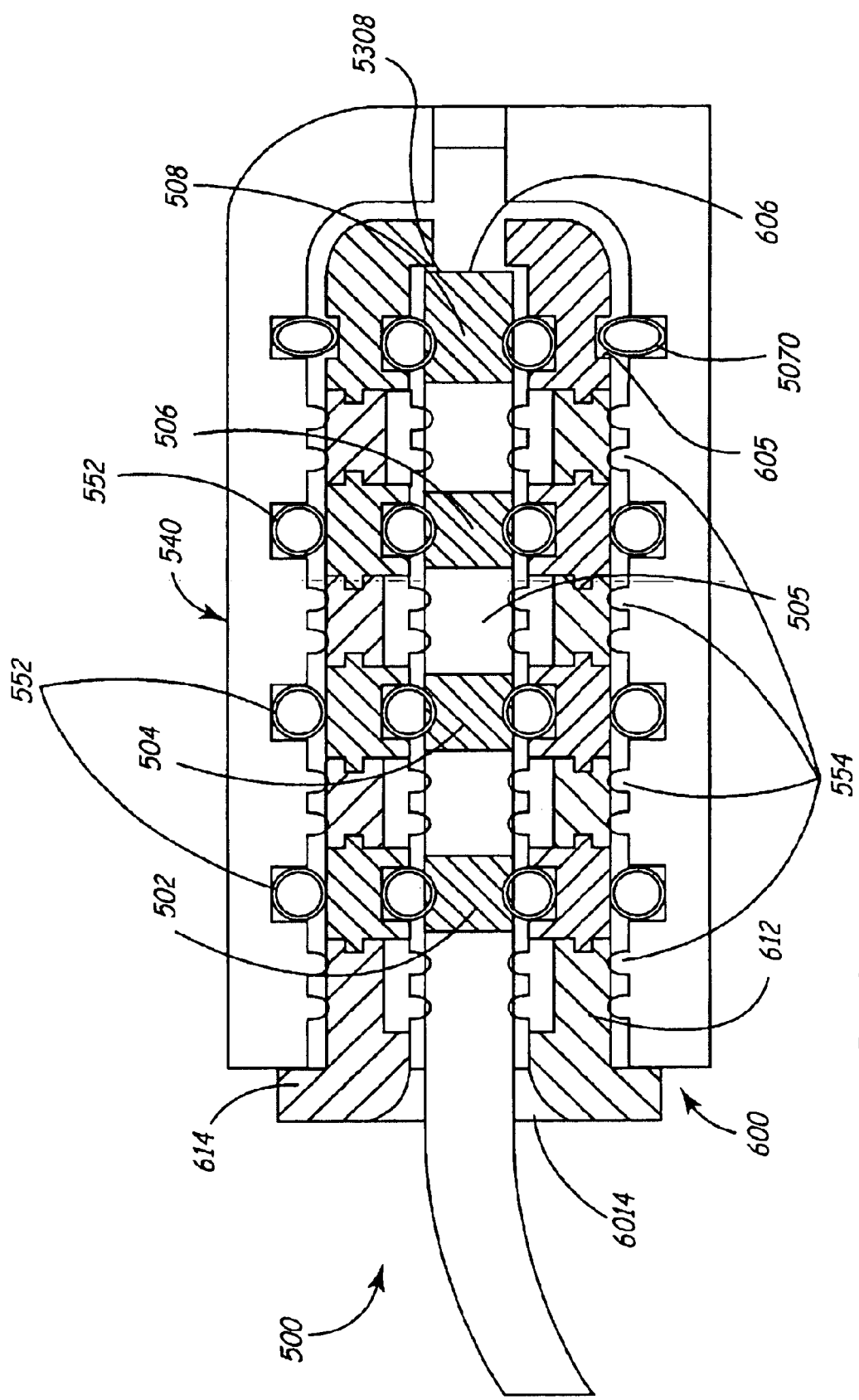
FIG. 13, a side cut-away view of the lead proximal end of FIG. 12A coupled to the connector block of the medical device of FIG. 12A, via the upsizing sleeve of FIG. 12A.

FIG. 13, a side cut-away view of lead proximal end 500 coupled to connector block 540 of medical device 580 (FIG. 12A) via upsizing sleeve 600. FIG. 13 illustrates the means for electrical connection between connector rings 502, 504, 506, and 508 of lead proximal end 500 and multiple electrical contacts 552 of connector block port 540 of device 580, via contact members 601, 602, 603, and 604 of upsizing sleeve 600. Electrical contacts 552 may be canted coil springs, such as the type of spring contacts available from Balseal, Inc., Foothill Ranch, Calif. Alternatively, electrical contacts 552 may be provided as other types of spring contacts or other types of contacts such as set-screws, or multi-beam contacts. Inner sealing rings 554 ensure electrical isolation between each of the contacts 552 which are electrically coupled to one of contact members 601, 602, 603 and 604. Contact member pitch, that is a center-to-center axial distance, may be between approximately 4.3 mm and 4.7 mm. Port 550 may include aspects as generally disclosed in U.S. Pat. No. 5,070,605 to Daglow et al., and U.S. Pat. No. 5,076,270 to Stutz. Jr., both of which patents are incorporated herein by reference in their entirety.

It should be noted that fewer seal members 610 and fewer spring contacts 622 than those shown in FIGS. 12C–13 may be employed for lead proximal ends having fewer connector rings; for example, with reference to FIG. 11A, a proximal end having a plurality of connector rings including only connector rings 506 and 508 may be coupled to a medical device with an upsizing sleeve having spring contacts 622 residing only within contact members 603 and 605 and seal members 610 residing within only insulation members 607 and 608 or 609 or distal portion 612. Thus, spring contacts 622 and seal members 610 may be employed within upsizing sleeve only where necessary, according to a number of connector rings provided by a proximal end of a particular type of lead, to ensure electrical coupling and isolation for that particular type. Likewise an additional embodiment of the present invention includes an upsizing sleeve having a greater number of spring contacts 622 and seal members 610, than that illustrated herein, in conjunction with a lead proximal end having a greater number of connector rings.

Port 550 may further include a retention member 570. Retention member 570 aids in retaining upsizing sleeve 600 within port 550. Retention member 570 may take the form of a set-screw, as illustrated in FIG. 12B, or other mechanical retention member such as a spring or a clip. Retention member 570 may also double as an electrical contact.

As further illustrated in FIG. 12C, contact member 604 includes a lip 606 and a retention groove 605. FIG. 13 illustrates interfaces with lip 606 and retention groove 605. As shown in FIG. 13, when lead proximal end 500 is fully inserted into lumen 616, a leading edge 5308 will butt up against lip 606, thus lip 606 provides a mechanical stop to prevent over-insertion of the lead as well as tactile feedback to a physician inserting the lead. As also shown in FIG. 13, a most proximal electrical contact 5070 provided in connector block port 550 doubles as a retention member engaging retention groove 605 when the upsizing sleeve 600 is fully inserted into port 550. It should be noted that a retention groove may be formed anywhere along an external surface of upsizing sleeve 600 for a corresponding retention member positioned in port 550.

Knob 614 is illustrated in FIG. 13 as a generally annular, radially outward extension of distal portion 612, being formed around a tapered distal opening 6014 of upsizing sleeve 600. Knob 614 is shown butted up against connector block 540 when sleeve 600 is fully inserted into connector block port 550. Knob 614 aids in insertion and removal of sleeve 600 into, and out from port 550 by providing an enlarged grip zone. In other embodiments, distal portion 612 may be provided without knob 614. Tapered distal opening 6014 provides strain relief for lead proximal end 500 where it exits sleeve 600; any form of enlarged opening such as one created with a rounded edge will perform the same function. In other embodiments, alternate forms of strain relief may be employed; one such alternate will be described below in conjunction with FIG. 23.

Figure 14A:
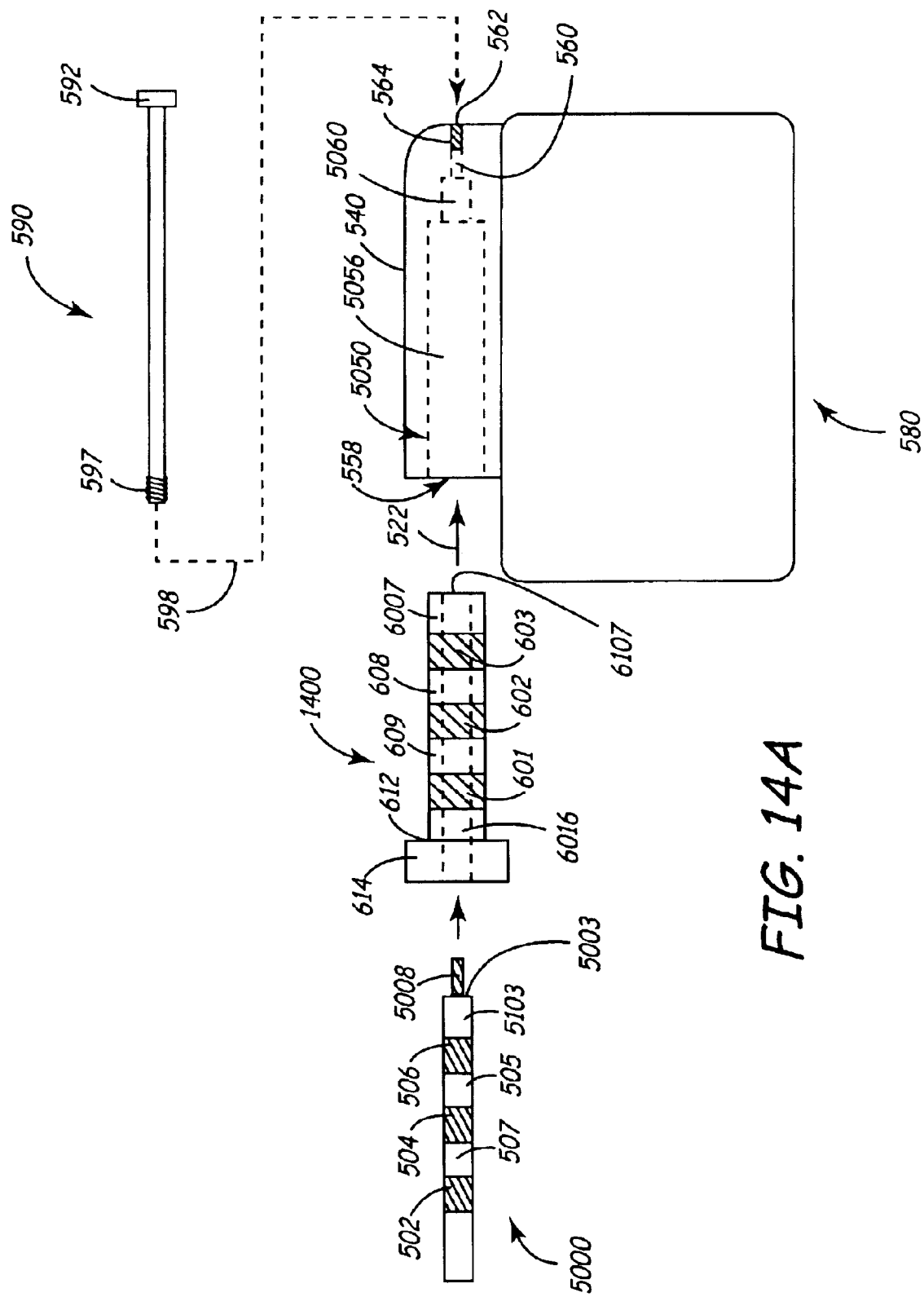
FIG. 14A is a plan view of an alternate embodiment of an upsizing sleeve.

FIG. 14A is a plan view of an alternate embodiment of an upsizing sleeve 1400 and further illustrates the manner in which upsizing sleeve 1400 may be used for coupling proximal end 5000 of a multi-polar lead to a medical device 580. Upsizing sleeve 1400, a generally tubular member having an inner lumen 6016, as indicated by dashed lines, is adapted to receive lead proximal end 5000 shown in FIG. 11B or proximal end 5000' shown in FIG. 11C or proximal end 5000" shown in FIG. 11D.

As illustrated in FIG. 14A, upsizing sleeve 1400, having a lumen 6016, includes conductive ring members 601, 602, and 603, separated by relatively rigid insulation members 608 and 609, a most proximal insulation member 6007, and distal portion 612 including knob 614. Conductive ring members 601, 602, and 603 enable electrical connection of one or more of connector rings 502, 504, 506. When proximal end 5000 is fully inserted into lumen 6016 of upsizing sleeve 1400, contact members 601, 602, and 603 will be aligned with connector rings 502, 504, and 506, respectively, and connector pin 5008 will extend proximally from a proximal opening 6107 for a predetermined length. Relatively rigid insulation members 608 and 609, along with most proximal insulation member 6007 and distal portion 612 provide means for a fluid tight seal about proximal end 5000 within lumen 6016. Conductive ring members 601, 602 and 603, insulation members 608 and 609, most proximal insulation member 6007, and distal portion 612 together form portions of an external surface of upsizing sleeve 1400 which conforms to predetermined dimensions corresponding with a connector block port 5050, indicated by dashed lines, which may be an industry standard connector block port. A diameter of the external surface of upsizing sleeve 1400 may be between approximately 3 mm and 3.5 mm. Connector block 540, as illustrated in FIG. 12A is shown in FIG. 14A to include port 5050 having a first lumen 5056 continuous with a second lumen 5060, which is continuous with smaller diameter lumen 560. Port 5050 will be further described herein in conjunction with FIG. 14B. Methods using upsizing sleeve 1400 to couple lead proximal end 5000 to port 5050 are similar to those described for sleeve 600 in conjunction with FIG. 12A.

Figure 14B:
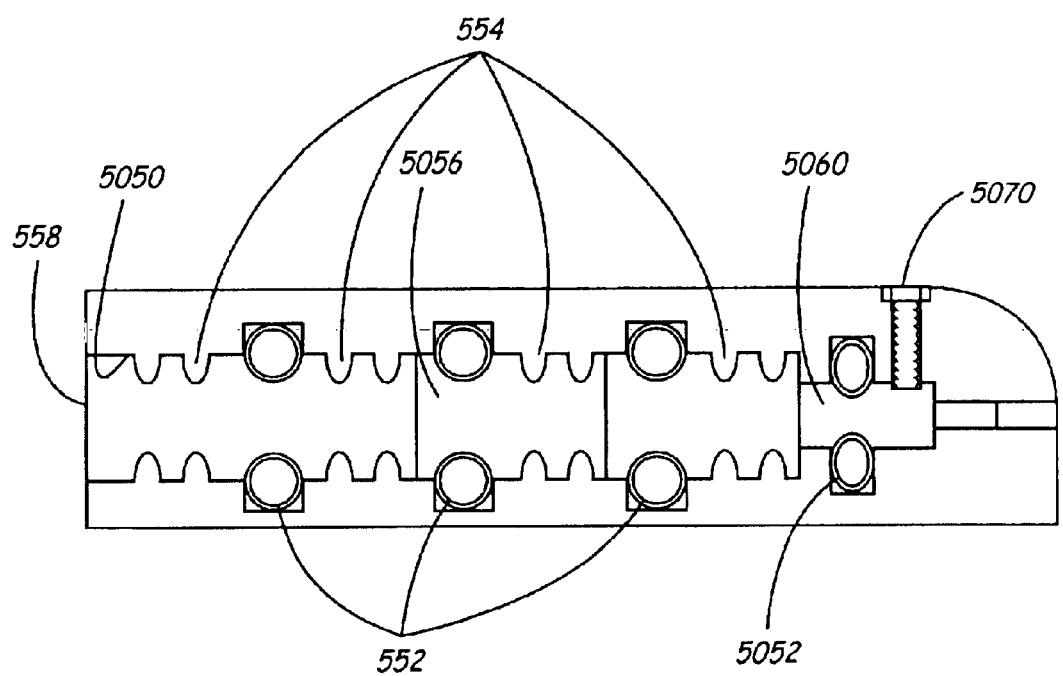
FIG. 14B is a side cut-away view of the connector block port of FIG. 14A.
Figure 15:
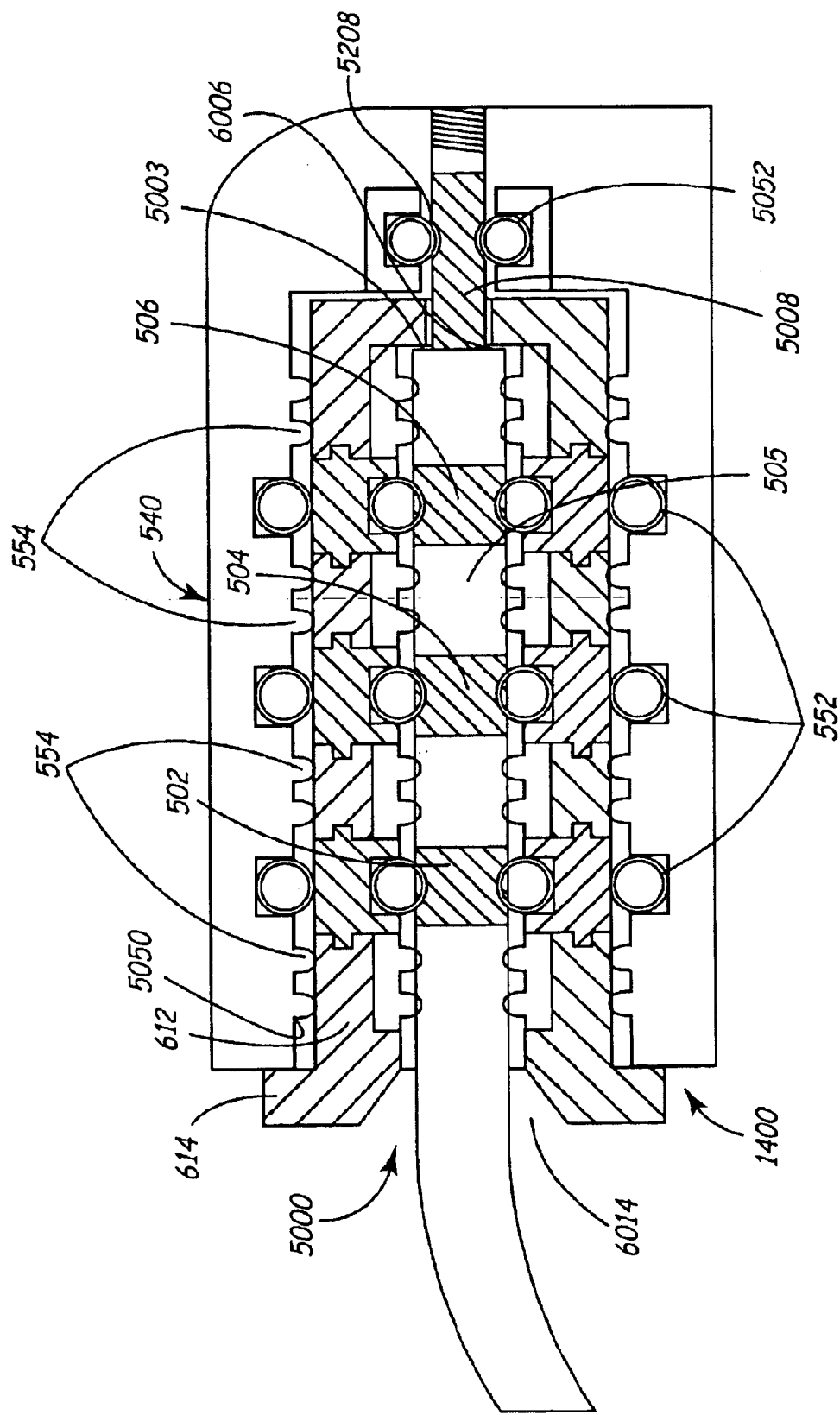
FIG. 15 is a side cut-away view of the lead proximal end of FIG. 14A coupled to the connector block of the medical device of FIG. 14A via the upsizing sleeve of FIG. 14A.

FIG. 14B is a side cut-away view of connector block port 5050. Port 5050 is an exemplary port of the type that may be used in conjunction with upsizing sleeve 1400. First lumen 5056 receives upsizing sleeve 1400 through opening 558 and second lumen 5060 receives connector pin 5008 extending proximally from upsizing sleeve 1400. As illustrated in FIG. 14B, port 5050 includes multiple electrical contacts 552 alternating with inner sealing rings 554 in first lumen 5056 and an electrical contact 5052 in second lumen 5060. Electrical contacts 552 are aligned with contact members 601, 602 and 603 of upsizing sleeve 1400 and electrical contact 5052 is aligned with connector pin 5008, and inner sealing rings 554 provide a fluid tight seal with upsizing sleeve 1400 by interfacing with insulation members 6007, 608, 609 and distal member 612, when lead proximal end 5000 is fully inserted in upsizing sleeve 1400, and upsizing sleeve 1400 is fully inserted into port 550, as illustrated in FIG. 15. Contact member pitch, that is a center-to-center axial distance, may be between approximately 4.3 mm and approximately 4.7 mm.

Port 550 may further include a retention member 5070. Retention member 5070 aids in retaining lead proximal end 5000 and upsizing sleeve 1400 within port 5050. Retention member 5070 may take the form of a set-screw, as illustrated in FIG. 14B, or other mechanical retention member such as a spring or a clip.

Figure 14C:
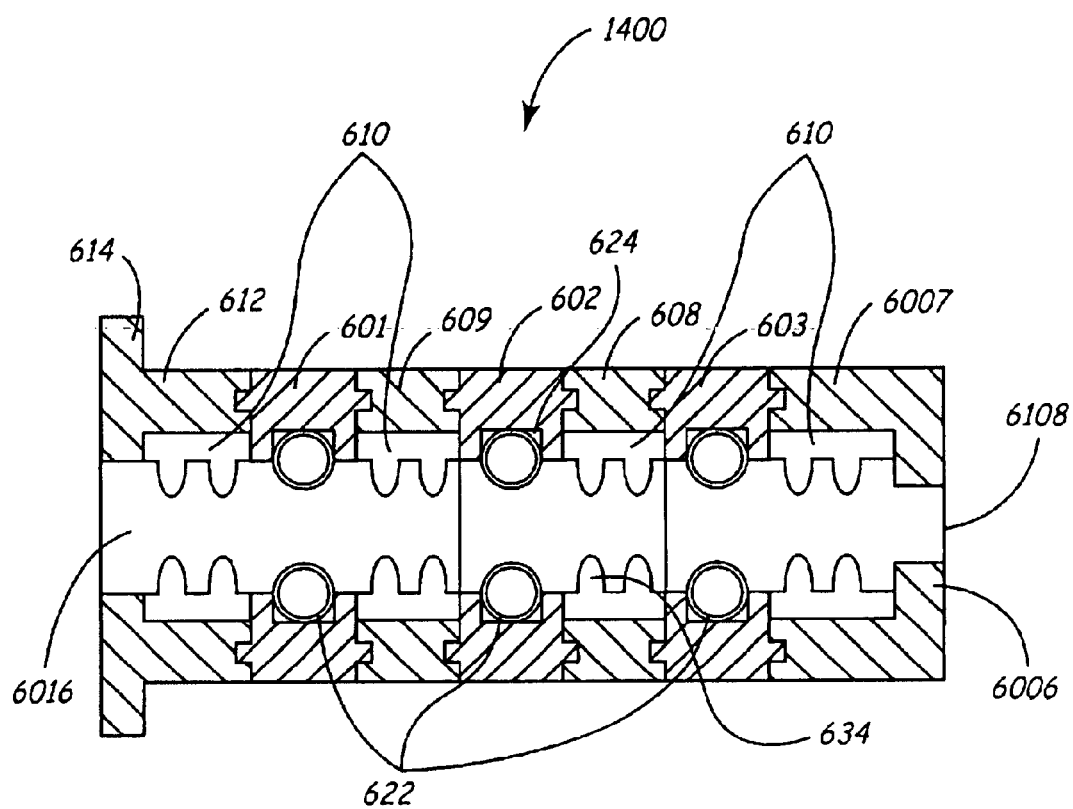
FIG. 14C is a side cut-away view of the upsizing sleeve of FIG. 14A.
Figure 14D:
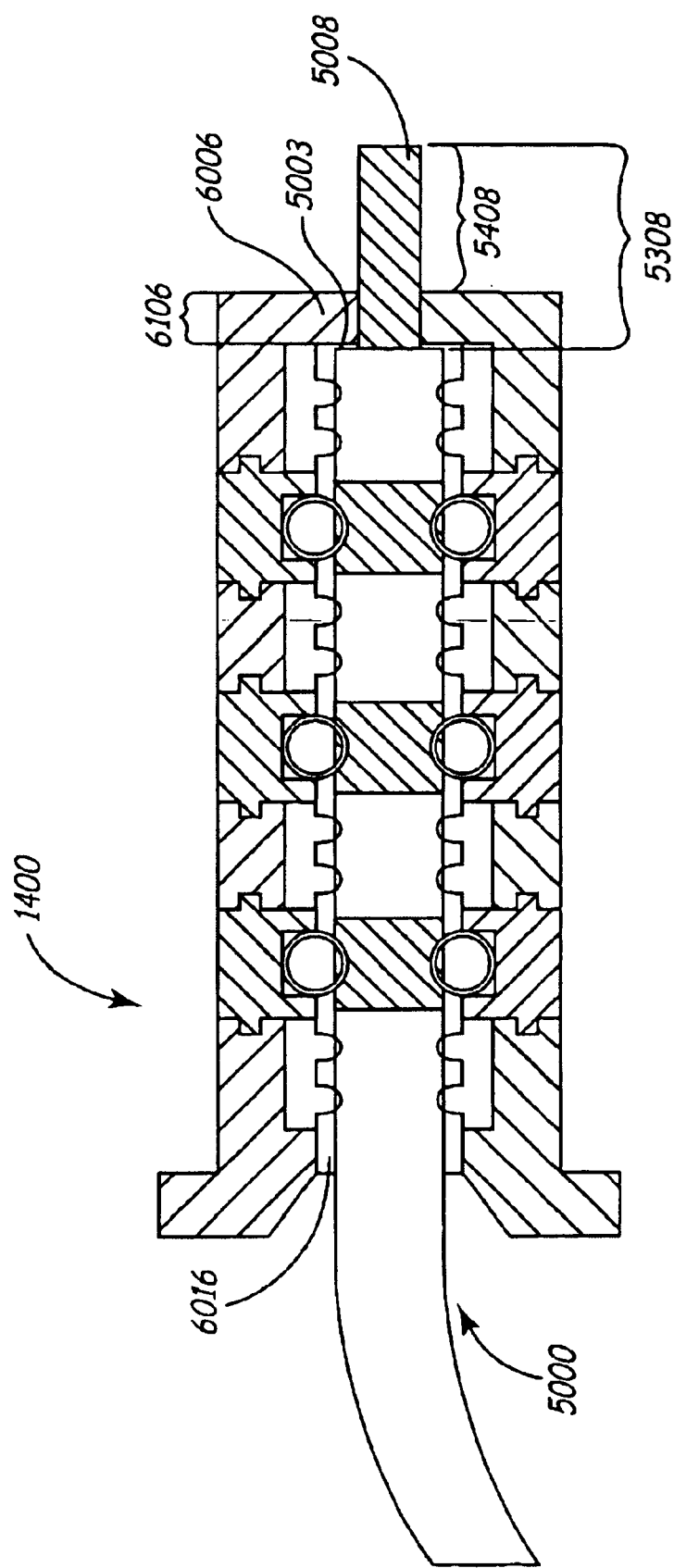
FIG. 14D is a side cut-away view of the lead proximal end engaged within an inner lumen of the upsizing sleeve, both of FIG. 14A.

FIG. 14C is a side cut-away view of upsizing sleeve 1400. The inner lumen 6016 for receiving proximal lead end 500 is generally formed by electrical contact members 601, 602 and 603, alternating with insulation members 6007, 608, 609, and distal portion 612. As illustrated in FIG. 14C, a seal member 610 resides within an inner surface of each insulating member 6007, 608, 609, and distal portion 612, and a coil spring contact 622 resides within an inner surface of each contact member 601, 602, 603, 604. Seal members 610 engage lead proximal portion 5000, as illustrated in FIG. 14D, to ensure electrical isolation between an electrical coupling of each of the contact members 601, 602 and 603 with each of the connector rings 502, 504 and 506, and to ensure electrical isolation between an electrical coupling of contact 5052 of port 5050 with connector pin 5008 and contact member 603 with connector ring 506 (FIG. 15).

As further illustrated in FIG. 14C, most proximal insulating member 6007 includes a lip 6006 and a proximal opening 6108. FIG. 14D is a side cut-away view of lead proximal end 5000 engaged within inner lumen 6016 of upsizing sleeve 1400. FIG. 14D illustrates an interface with lip 6006, according to one embodiment of the present invention. As shown in FIG. 14D, when lead proximal end 5000 is engaged within lumen 6016, a leading edge 5003 will butt up against lip 6006. Lip 6006 has a thickness 6106 corresponding with a length 5308 of connector pin 5008 such that when lead proximal end 5000 is engaged within upsizing sleeve 1400 a predetermined length 5408 of connector pin 5008 extends beyond proximal opening 6106, as illustrated in FIG. 14D. Thus lead proximal end 5000 engaged within upsizing sleeve 1400 conforms to predetermined dimensions, which may conform to an industry standard, for coupling within port 5050 of medical device 580 (FIG. 14A). In an alternate embodiment proximal end 5000 may be generally isodiametric and a groove similar to retention groove 5208 illustrated in FIG. 11B may be incorporated to interface with lip 6106 of upsizing sleeve 1400 to assure predetermined length 5408 of connector pin 5008 extending beyond proximal opening 6106. Predetermined length 5408 may be between approximately 5 mm and approximately 6.4 mm. A diameter of pin 5008 may be between approximately 1 mm and 1.7 mm.

FIG. 15 is a side cut-away view of lead proximal end 5000 coupled to connector block 540 of medical device 580 (FIG. 14A) via upsizing sleeve 1400. FIG. 15 illustrates the means for electrical connection between connector rings 502, 504 and 506, of lead proximal end 5000, and multiple electrical contacts 552 of connector block port 5050 of device 508, via contact members 601, 602 and 603 of upsizing sleeve 1400. FIG. 15 further illustrates a direct electrical connection between lead connector pin 5008 and electrical contact 5052 of connector block port 5050. Electrical contacts 552 may be canted coil springs, such as the type of spring contacts available from Balseal, Inc., Foothill Ranch, Calif. Alternatively, electrical contacts 552 may be provided as other types of spring contacts or other types of contacts such as set-screws, or multi-beam contacts. Inner sealing rings 554 ensure electrical isolation between each of the contacts 552 and 5052, which are electrically coupled to one of contact members 601, 602 and 603 and connector pin 5008, respectively. Port 5050 may include aspects as generally disclosed in U.S. Pat. No. 5,070,605 to Daglow et al., and U.S. Pat. No. 5,076,270 to Stutz. Jr., both of which patents are incorporated herein by reference in their entirety.

FIG. 15 further illustrates contact 5052 doubling as a retention member by interfacing with retention groove 5208 of connector pin 5008. Groove 5208 is not a necessary feature if set-screw retention member 5070 is incorporated in port 5050. In alternate embodiments, a retention groove may be formed on upsizing sleeve 1400 to interface with a retention member in a manner similar to that illustrated for upsizing sleeve 600 in FIG. 13.

It should be noted that fewer seal members 610 and fewer spring contacts 622 than those shown in FIGS. 14C–15 may be employed for lead proximal ends having fewer connector rings; for example, with reference to FIG.11C, proximal end 5000' having a plurality of connector rings including only connector ring 506 may be coupled to a medical device with an upsizing sleeve having spring contact 622 residing only within contact member 603 and seal members 610 residing within only insulation members 6007 and 608 or 609 or distal portion 612. Thus, spring contacts 622 and seal members 610 may be employed within upsizing sleeve only where necessary, according to a number of connector rings provided by a proximal end of a particular type of lead, to ensure electrical coupling and isolation for that particular type. Likewise an additional embodiment of the present invention includes an upsizing sleeve having a greater number of spring contacts 622 and seal members 610, than that illustrated herein, in conjunction with a lead proximal end having a greater number of connector rings.

According to one embodiment of the present invention, FIG. 15 further illustrates knob 614 as a generally annular, radially outward extension of distal portion 612, being formed around a tapered distal opening 6014 of upsizing sleeve 600. Knob 614 is shown butted up against connector block 540 when sleeve 1400 is fully inserted into connector block port 550. Knob 614 aids in insertion and removal of sleeve 600 into, and out from port 550 by providing an enlarged grip zone. In other embodiments, distal portion 612 may be provided without knob 614. Tapered distal opening 6014 provides strain relief for lead proximal end 500 where it exits sleeve 600; any form of enlarged opening such as one created with a rounded edge will perform the same function. In other embodiments, alternate forms of strain relief may be employed; one such alternate will be described below in conjunction with FIG. 23.

Figures 16A, 16B:
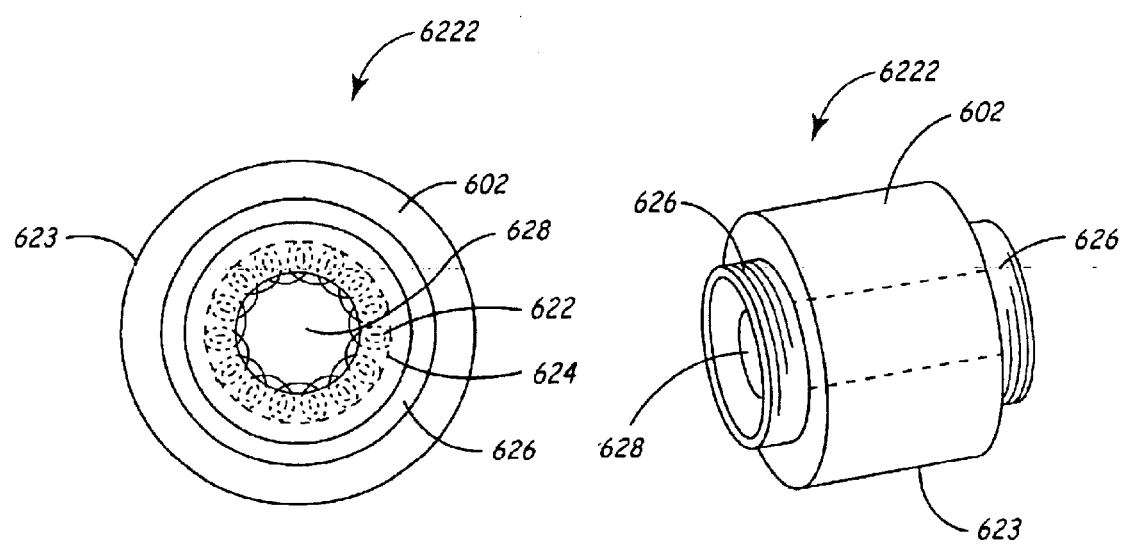
FIGS. 16A–B are an end, plan view and a perspective view, respectively, of an electrical contact assembly.
Figure 16C:
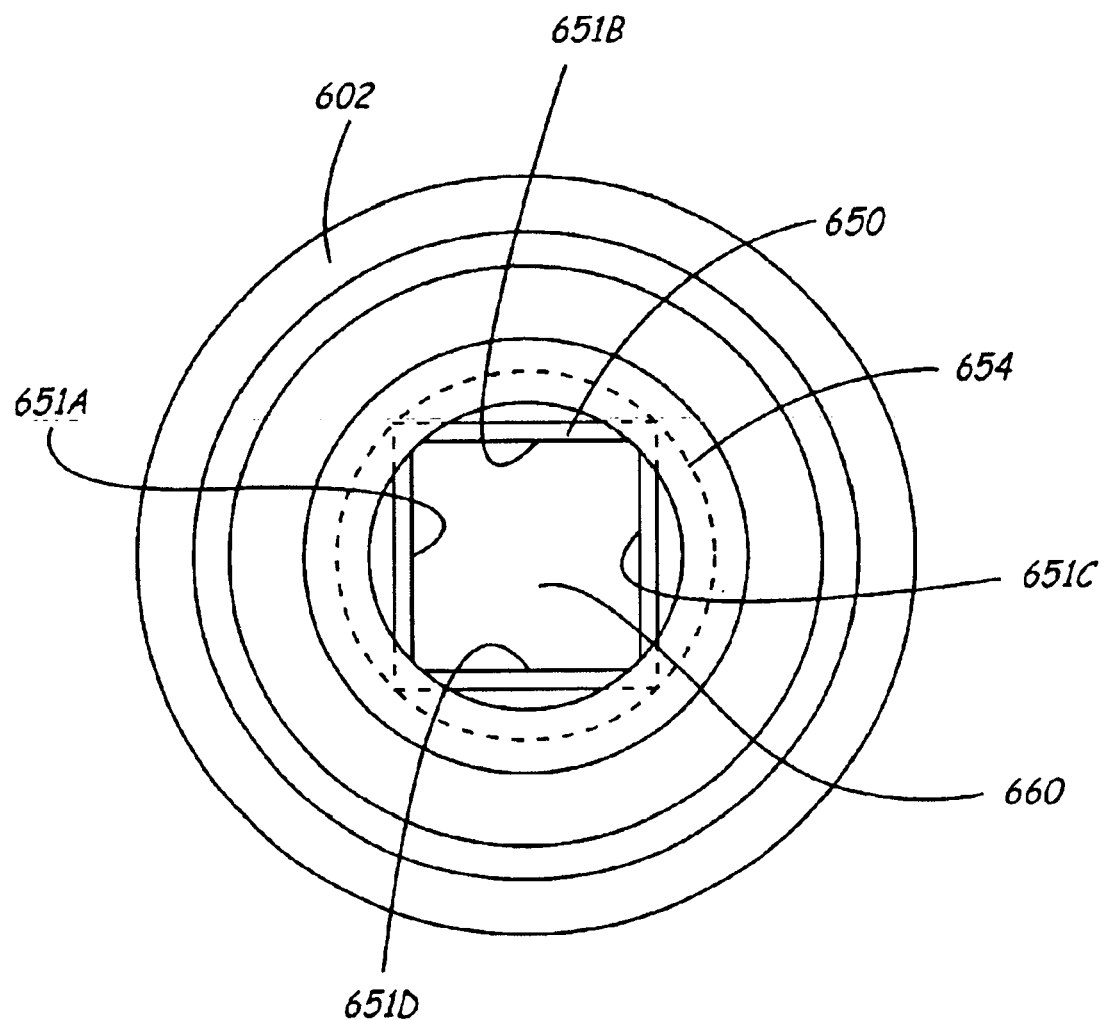
FIG. 16C is an end plan view of an alternate embodiment of a spring contact housed within contact member.

FIGS. 16A–B are an end, plan view and a perspective view, respectively, of an electrical contact assembly 6222. As illustrated in FIGS. 16A–B, contact assembly 6222 includes contact member 602, having an outer surface 623, annular flanges 626, and an inner surface forming an annular channel 624, indicated by a dashed line, and coil spring contact 622 being housed within annular channel 624. Outer surface 623 forms a portion of an external surface of upsizing sleeve 600 or 1400. According to one embodiment of the present invention, flanges 626, extending axially from both ends of contact member 602, as illustrated in FIG. 16B, serve as mating interfaces for joining contact member 602 with adjacent insulation members 608 and 609 (FIGS. 12C and 14C) as will be described below. Flanges 626 may be threaded. Channel 624 may be generally rectangular in cross-section as shown in FIGS. 12C and 14C. Coil spring contact 622, inserted within channel 624, forms an inner lumen 628 making circumferential electrical contact with a connector ring, such as connector ring 504 as illustrated in FIGS. 13 and 15, when, for example, lead proximal end 500 or 5000 is engaged within upsizing sleeve 600 or 1400, respectively. Coil spring contact 622 may be a canted coil spring contact of the type commercially available from Balseal, Inc. Contact member 602 may be machined from a conductive material, such as stainless steel, titanium, platinum/iridium, or a nickel alloy. In other embodiments, coil spring contact 622 may be replaced with other types of spring contacts or other types of contacts such as set-screws, multi-beam contacts, crushable contacts or otherwise. One such alternate embodiment of a spring contact according to the present invention is illustrated in FIG. 16C. FIG. 16C is an end plan view of a substantially square spring contact 650 housed within contact member 602. Spring contact 650, inserted within channel 654, forms an inner lumen 660 to make electrical contact, at points 651A, 651B, 651C, and 651C, with a connector ring, such as connector ring 504 as illustrated in FIGS. 13 and 15, when, for example, lead proximal end 500 or 5000 is engaged within upsizing sleeve 600 or 1400, respectively.

Figures 17, 18:
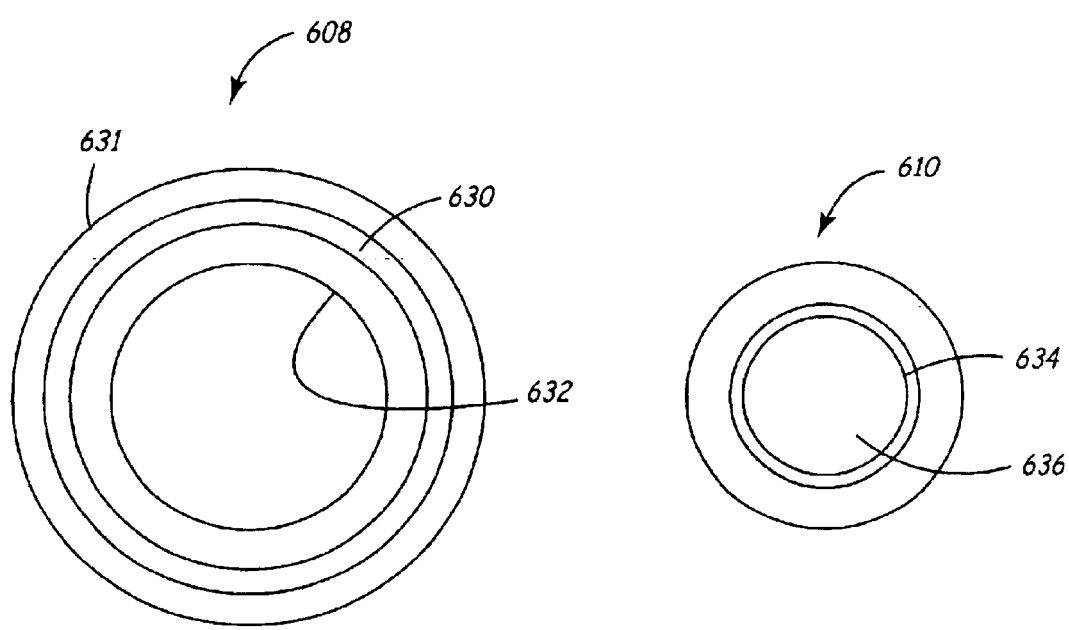
FIG. 17 is an end, plan view of an insulation member.
FIG. 18 is an end, plan view of a seal member.

FIG. 17 is an end, plan view of insulation member 608. As illustrated in FIG. 17, insulation member 608 includes an outer surface 631, an annular groove 630 and an inner surface 632, which serves to house seal member 610. Outer surface 631 forms a second portion of external surface of upsizing sleeve 600 or 1400, being approximately equal in diameter to that of outer surface 623 of contact member 602. According to one embodiment of the present invention, annular groove 630, sized to receive flange 626 of contact member 602, as illustrated in FIG. 16B, serves as a mating interface for joining with contact member 602 (FIGS. 12C and 14C) as will be further described below. If flange 626 of contact member 602 is threaded, groove 630 may be pre-threaded for mating with flange 626. Alternatively, groove 630 may be provided such that, as flange 626 is screwed into groove 630, mating threads in groove 630 are self-tapping. In other embodiments, flange 626 and groove 630 may interlock in a press-fit and/or be joined by an appropriate adhesive bonding method.

FIG. 18 is an end, plan view of seal member 610. Seal member 610 is provided with one or more inner protrusions 634 forming an inner lumen 636. (Inner protrusions are shown in section view of FIG. 14C.) In one embodiment of the present invention, seal member 610 is sized to fit within inner surface 632 of insulation member 608 in order that inner lumen 636 of seal member 610 may provide a fluid tight seal about an insulative spacer, such as spacer 505 as illustrated in FIGS. 13 and 15, when, for example, lead proximal end 500 or 5000 is engaged within upsizing sleeve 600 or 1400, respectively. Insulation member 608 may be formed from a ceramic, an epoxy, or a relatively rigid thermoplastic, such as polyurethane, polysulfone, PEEK, or any combination thereof, and seal member may be formed from an elastomer such as silicone rubber.

Figure 19A:
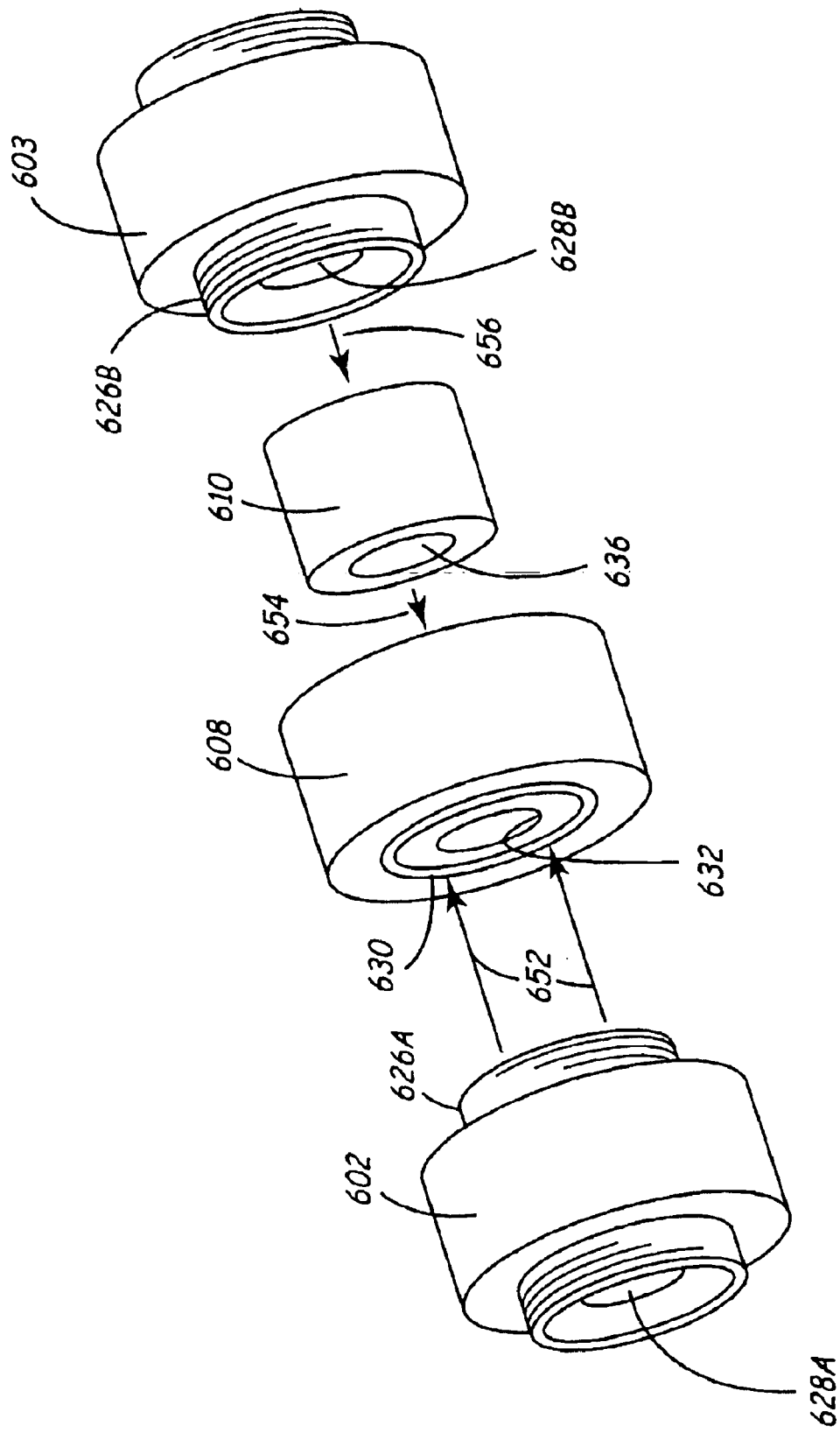
FIG. 19A is a schematic illustrating one method, according to the present invention, of assembling components included, for example, in an upsizing sleeve of FIG. 12C or 14C.

FIG. 19A is a schematic illustrating one method, according to the present invention, of assembling components included, for example, in upsizing sleeve 600 or 1400. Upsizing sleeve 600 or 1400 may be assembled by joining individual insulation members, for example 608 and 609, with contact members, for example 602 and 603, via mating interfaces, in an alternating fashion. In one embodiment according to the present invention and illustrated in FIG. 19A, the mating interfaces include flange 626A and groove 630; contact member 602 may be joined with insulating member 608 by inserting flange 626A into groove 630, as indicated by arrows 652. If flange 626A is threaded, contact member 602 may be rotated relative to insulating member 608 such that contact member 602 and insulating member 608 are screwed together. Flange 626A and groove 630 may alternatively be press fit together. In other methods for assembling upsizing sleeve 600, an adhesive may be applied to groove 630 and/or flange 626A prior to inserting flange 626A into groove 630. Alternately, another embodiment according to the present invention employs substantially flat mating interfaces, of insulating member 608 and contact member 602, joined by an adhesive bond. If insulating member 608 is made from a polyurethane, a primer comprising a solvent, such as DMAC, combined with a polyurethane base material may be used to prep mating interfaces, for example groove 630, prior to bonding with a polyurethane adhesive. Additionally a sealing filler, not shown, such as silicone adhesive may be applied between mating interfaces.

Spring contacts 622, 650 are typically inserted into annular channels 624, 654 of contact members 602 and 603 before joining with insulating member 608. (FIG. 16A) (Alternately, an upsizing sleeve such as upsizing sleeve 1400 (FIG. 14C) requires only one spring coil contact 622 inserted within annular channel 624 of contact member 603 for coupling a proximal end of a lead, such as proximal end 5000' (FIG. 11C).) Seal member 610 is inserted within inner surface 632 of insulating member 608 as indicated by arrow 654 either before or after joining contact member 602 and insulating member 608. (Alternately, an upsizing sleeve such as upsizing sleeve 1400 (FIG. 14C) may not require seal member 610 inserted within insulating member 608 for coupling a proximal end of a lead, such as proximal end 5000' (FIG. 11C); in this case a seal member 610 is required within most proximal insulating member 6007 and any one of the other insulation members 608, 609, or distal portion 612.) Seal member 610 may form a high-interference interface with the inner surface of insulating member 608 and be held in place by such an interference fit; alternately, an adhesive bond may be formed between seal member 610 and inner surface 632 of insulating member 608. If insulating member 608 is made from polyurethane, a primer, such the one described above, may be used to prep an interface between seal member 610 and inner surface 632 for a polyurethane or silicone adhesive bond. Alternately, if insulating member 608 is made from polysulfone, a primer such as Shin-etsu X65-196 available from Technical Resin Packaging in Brooklyn Park, Minn. may enhance a silicone bond between seal member 610 and inner surface 632. Next, a second contact member 603 may be joined to insulating member 608 in the manner described above for joining first contact member 602 to insulating member 608. Inner lumens 628A and 628B of contact members 602 and 603, respectively, are now aligned with inner lumen 636 of seal member 610, and together form a segment of lumen 616 of upsizing sleeve 600.

According it one embodiment of the present invention, to complete the assembly of upsizing sleeve 600, additional insulation members and contact members may be joined in an alternating manner with proximal contact member 604 added as the final contact and distal portion 612 added as the final insulating member (FIG. 12C). Likewise for upsizing sleeve 1400, with most proximal insulating member 6007 and distal portion 612 terminating either end (FIG. 14C).

It is recognized that any number of desired contact members and insulation members may be assembled to form a multipolar upsizing sleeve. Furthermore, insulation members and contact members may be assembled in any logical order, for example beginning with distal portion 612 that is joined to contact member 601, followed by insulating member 609 and contact member 602, and so forth until ending with proximal contact member 604 or most proximal insulating member 6007. Alternatively, assembly may begin with either proximal contact member 604 or most proximal insulating member 6007, working back to distal portion 612, or assembly may begin with any intervening insulation members and contact members working outward.

Figure 19B:
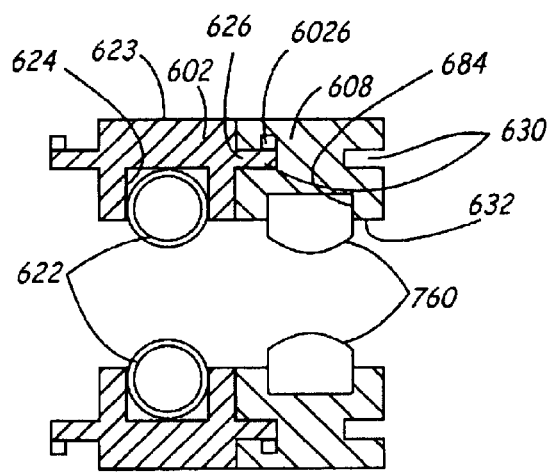
FIGS. 19B–D are side, cut-away views of a partially assembled upsizing sleeves.
Figure 19D:
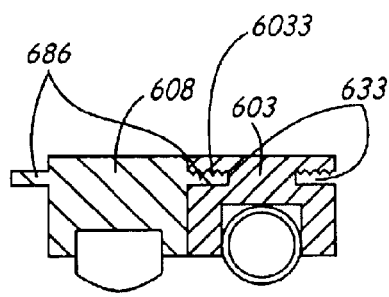
Figure 19C:
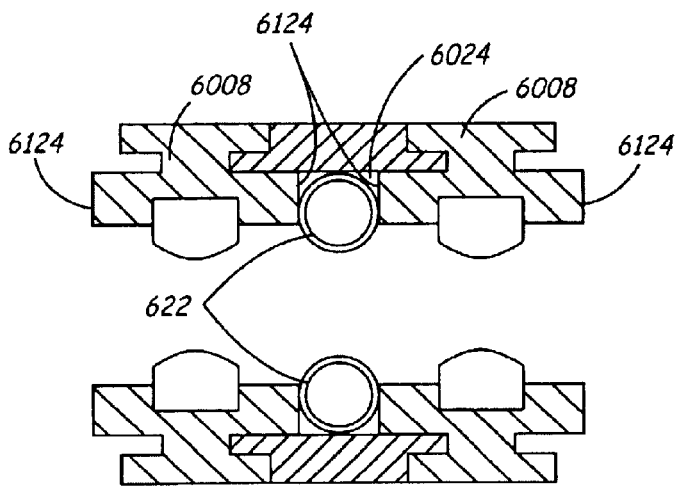

FIGS. 19B–D are side, cut-away views of a partially assembled upsizing sleeves. According to an embodiment of the present invention, FIG. 19B illustrates inner surface 632 of insulating member 608 including an annular channel 684 for housing an O-ring type sealing member 760. Annular channel 684 may also house previously described seal member 610. Either a press fit or an adhesive bond may be formed between sealing member 760, 610 and annular channel 684. FIG. 19B further illustrates flanges 626 including radial extensions 6026, interlocking within annular grooves 630, according to another embodiment of mating interfaces of the present invention. Although extensions 6026 are shown projecting outward, toward outer surface 623 of contact member 602, they may alternately project inward. FIG. 19C illustrates an alternate embodiment according to the present invention wherein an annular channel 6024 for spring contact 622 is formed by side-wall surfaces 6124 of insulating members 6008.

FIG. 19D illustrates another embodiment according to the present invention wherein insulating member 608 includes flanges 686 and contact member 603 includes annular grooves 633 forming mating interfaces opposite of those described in conjunction with FIGS. 16A–19B. As illustrated in FIG. 19D, a mating interface of flange 686 and groove 633 further includes threads 6033; contact member 603 may be rotated relative to insulating member 608 such that contact member 603 and insulating member 608 are screwed together. Flange 686 and groove 633 may alternatively be press fit together and, or an adhesive may be used as described in conjunction with FIG. 19A. It should be noted that flanges and grooves of mating interfaces, according to the preceding discussion, need not extend around the full circumference of contact members and insulation members in every embodiment of the present invention.

Figure 21:
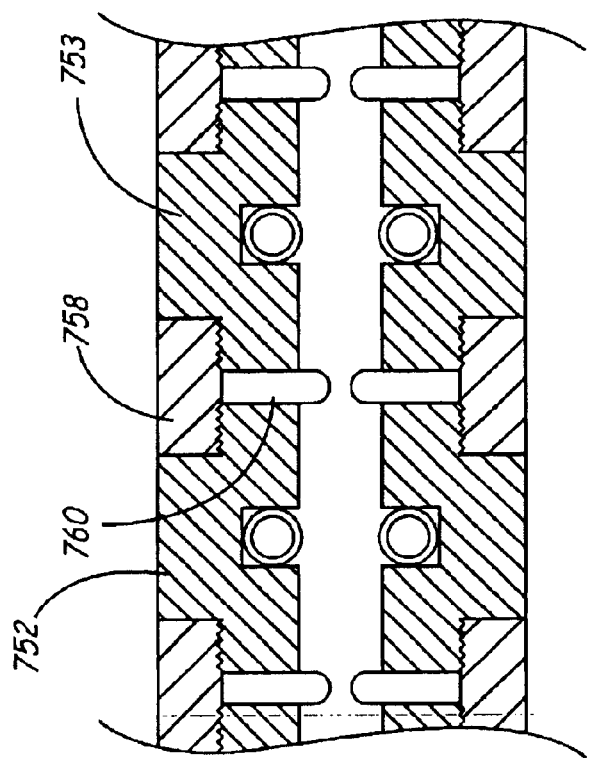
FIGS. 20–21 are a side, cut-away views of sections of various alternate mating interfaces for an upsizing sleeve according to the present invention.
Figure 20:
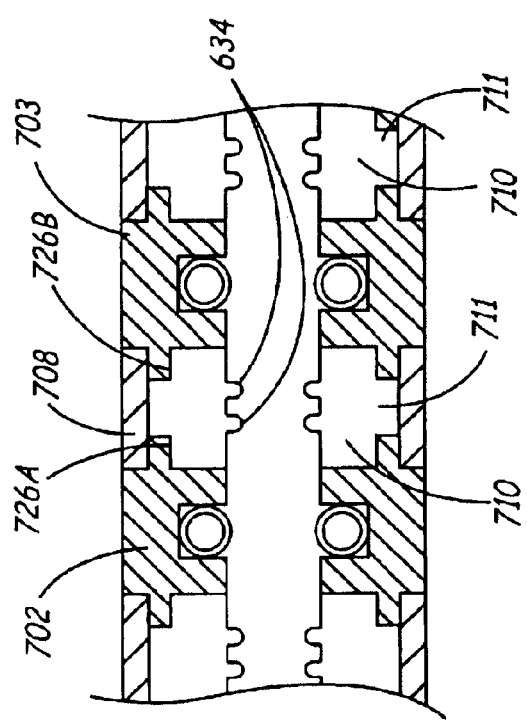

FIGS. 20–21 are a side, cut-away views of sections of various alternate mating interfaces for an upsizing sleeve according to the present invention. As illustrated in FIG. 20, insulating member 708 is generally ring shaped having surfaces overlapping on mating surfaces of flanges 726A and 726B of contact members 702 and 703, respectively. FIG. 20 further illustrates threaded engagement of mating surfaces, however an adhesive bond between surfaces is an alternative, or may be in addition to the threaded interface; a sealing filler may alternately be used in addition to the threaded interface. A seal member 710, is shown to have an annular, radially outward extension 711 that may be generally rectangular in cross-section and is captured between the end faces of flanges 726A and 726B. Seal member 710 is captured between contact members 702 and 703 when they are joined with intervening insulating member 708, according to one embodiment of the present invention. As illustrated in FIG. 21, O-ring type sealing member 760 is captured between two contact members 752 and 753 that are joined to an intervening generally ring-like insulating member 758, in alternative manners similar to those described in conjunction with FIG. 20.

FIGS. 22A–B are a side, cut-away views of sections of various additional mating interfaces, having overlapping surfaces, for an upsizing sleeve according to alternate embodiments of the present invention. As illustrated in FIG. 22A, an insulating member 768 is provided with a cross-section that is generally "T" shaped. Overlapping surfaces of insulating member 768 includes radially-inward extensions 766A and 766B that interlock with underlying surfaces of contact members 762 and 763 having radially-outward extensions 764A and 764B. As illustrated in FIG. 22B, contact members 782 and 783 are provided with generally "T" shaped cross-sections. Overlapping surfaces of contact members 782 and 783 include radially inward projections 784A and 784B that interlock with underlying surfaces of an insulating member 788 having radially-outward projections 786A and 786B. These mating interfaces may further include adhesive bonds and/or sealing fillers. Alternately both sets of radial extensions may be excluded from mating interfaces and an adhesive bond and, or threaded interface provided instead. Furthermore, it should be noted that insulating member 768 of FIG. 22A and insulating member 788 of FIG. 22B may have inner surfaces including annular channels to house seal members, as illustrated in FIGS. 19B–C.

An alternate method according to the present invention, of assembling components included, for example, in upsizing sleeve 600 or 1400, includes an over-molding process. Referring to FIG. 22A, contact members 762 and 763 and seal members 770 and 771, or any desired number of contact members and seal members, may be loaded onto a mandrel with seal members positioned between contact members. The mandrel may then be mounted into a mold. A thermoplastic, such as polyurethane, polysulfone, or PEEK may be injection molded into the vacant volumes within the mold to form insulation members 768. Alternatively, the insulation members 768 may be formed by casting of a thermoset, such as epoxy, injected into the vacant mold volumes. An entire upsizing sleeve may be molded or cast in such a manner or subassemblies may be formed and then fitted together in a secondary process, similar to those described above, to complete an assembly of a sleeve.

While specific geometries of contact members, insulation members, and seals have been described and illustrated, it is recognized that numerous geometries of contact members, insulation members and seals may be possible for assembling an in-line, multipolar upsizing sleeve in accordance with the present invention. Assembly methods may include joining individually molded and machined components or over-molding techniques as described above.

Figure 23:
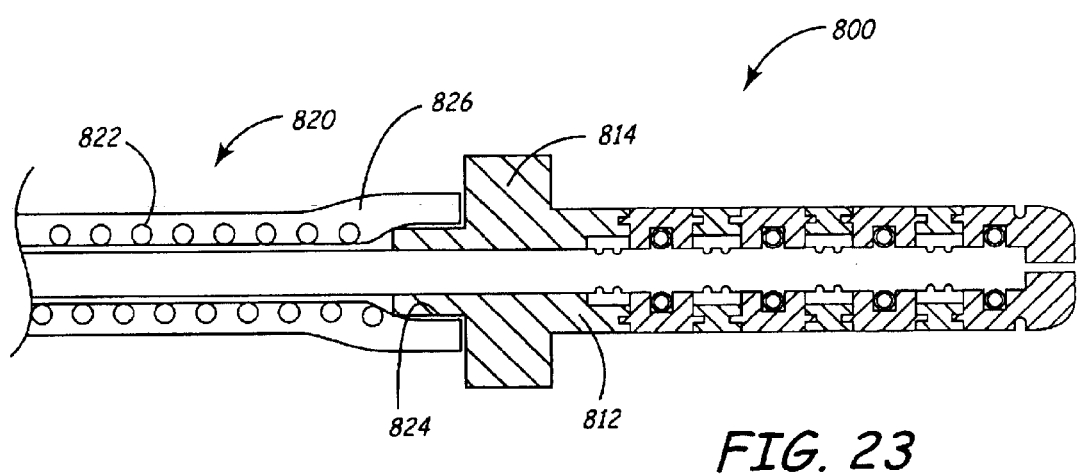
FIG. 23 is a side, cut-away view of an alternative embodiment of an upsizing sleeve having a strain relief sleeve.

FIG. 23 is a side, cut-away view of an alternative embodiment of an upsizing sleeve 800 having a strain relief sleeve 820 extending from distal insulating member 812. Strain relief member 820 acts to support the proximal lead end 500 where it exits distal insulating member 812 of sleeve 800. As illustrated in FIG. 23, strain relief sleeve 820 includes a tubular member 826 made of a flexible polymer and a reinforcing coil 822 made of a biocompatible metal such as a nickel-cobalt alloy or stainless steel. Strain relief member 820 may be joined to insulating member 812 by sliding the strain relief member 820 over an annular coupling flange 824, extending distally from the insulating member 812. An adhesive, such as silicone or polyurethane adhesive, may be used to bond strain relief member 820 to distal insulating member 812.

It should be noted that the inventive system and method of coupling a lead to a medical device as described and illustrated herein may be adapted for use with any size lead, any type of connector standard, and any type of medical device. For example, the up-sizing sleeve may be used with leads for drug delivery devices, devices adapted for neurological applications, or for any other type of physiological application requiring a lead coupled to an implantable or non-implantable device. Thus, many adaptations of the above-described invention will become apparent to one skilled in the art, and the description is therefore to be considered not as limiting, but as exemplary only.

We claim:

1. A system for coupling a medical electrical lead to a medical device comprising:

an upsizing sleeve, including an external surface, a plurality of contact members, a plurality of spring contacts, a plurality of relatively rigid insulation members, and a plurality of seal members;

the plurality of contact members including outer surfaces forming a first portion of the external surface of the upsizing sleeve, and inner surfaces housing corresponding spring contacts; and the plurality of relatively rigid insulation members including outer surfaces forming a second portion of the external surface of the upsizing sleeve, and inner surfaces housing corresponding seal members; wherein each of the plurality of contact members are joined in an alternating manner with each of the plurality of rigid insulation members.

2. The system of claim 1, wherein the inner surfaces of the insulation members form annular channels housing corresponding seal members.

3. The system of claim 1, wherein the insulation members further include side-wall surfaces forming annular channels housing corresponding spring contacts.

4. The system of claim 1, wherein the inner surfaces of the contact members form annular channels housing corresponding spring contacts.

5. The system of claim 1, wherein the plurality of insulation members of the upsizing sleeve is formed from polyurethane, polysulfone, PEEK, ceramic, or epoxy.

6. The system of claim 1, wherein the upsizing sleeve further comprises a distal end forming a distal opening including means for strain relief.

7. The system of claim 6, wherein the upsizing sleeve further comprises a knob being formed about the distal end.

8. The system of claim 6, wherein means for strain relief extends distally from the distal end.

9. The system of claim 1 further comprising:

a proximal end of the medical electrical lead including a plurality of connector rings, a plurality of insulative spacers, and a connector pin having a predetermined diameter and terminating the proximal end of the lead; wherein the upsizing sleeve further includes an internal surface forming a lumen to engage the proximal end of the lead and a proximal opening; wherein the external surface of the upsizing sleeve conforms to predetermined dimensions when the proximal end of the lead is engaged within the lumen of the upsizing sleeve; and the connector pin extends proximally from the proximal opening, for a predetermined length, when the proximal end of the lead is engaged within the lumen of the upsizing sleeve.

10. The system of claim 9, wherein the inner surfaces of the insulation members form annular channels housing corresponding seal members.

11. The system of claim 9, wherein the insulation members further include side-wall surfaces forming annular channels housing corresponding spring contacts.

12. The system of claim 9, wherein the inner surfaces of the contact members form annular channels housing corresponding spring contacts.

13. The system of claim 9, wherein:

the plurality of connector rings includes a first connector ring;

the plurality of insulative spacers includes a first insulative spacer positioned between the first connector ring and the connector pin;

the plurality of spring contacts includes a first spring contact to electrically engage the first connector ring when the proximal end of the lead is engaged within the lumen of the upsizing sleeve; and the plurality of seal members includes a first sealing member to provide a fluid tight seal about the first insulative spacer when the proximal end of the lead is engaged within the lumen of the upsizing sleeve.

14. The system of claim 13, wherein:

the plurality of connector rings further includes a second connector ring;

the plurality of insulative spacers further includes a second insulative spacer positioned between the first connector ring and the second connector ring;

the plurality of spring contacts further includes a second spring contact to electrically engage the second connector ring when the proximal end of the lead is engaged within the lumen of the upsizing sleeve; and the plurality of seal members further includes a second sealing member to provide a fluid tight seal about the second insulative spacer when the proximal end of the lead is engaged in the lumen of the upsizing sleeve.

15. The system of claim 9, wherein the connector pin terminating the proximal portion of the lead includes a retention groove.

16. A system for coupling a medical electrical lead to a medical device comprising:

a proximal end of the medical electrical lead including a plurality of connector rings, a plurality of insulative spacers, and a connector pin having a predetermined diameter and terminating the proximal end of the lead;

an upsizing sleeve, including an external surface, an internal surface forming a lumen to engage the proximal end of the lead, a proximal opening, a distal end forming a distal opening including a means for strain relief, a plurality of contact members, a plurality of spring contacts, a plurality of relatively rigid insulation members, and a plurality of seal members;

the plurality of contact members including outer surfaces forming a first portion of the external surface of the upsizing sleeve, and inner surfaces each comprising inner surfaces housing corresponding spring contacts; and the plurality of relatively rigid insulation members including outer surfaces forming a second portion of the external surface of the upsizing sleeve, and inner surfaces housing corresponding seal members; wherein each of the plurality of contact members are joined in an alternating manner with each of the plurality of rigid insulation ring members;

the external surface of the upsizing sleeve conforms to predetermined dimensions when the proximal end of the lead is engaged within the lumen of the upsizing sleeve; and the connector pin extends proximally from the proximal opening, for a predetermined length, when the proximal end of the lead is engaged within the lumen of the upsizing sleeve.

17. The system of claim 16, wherein the plurality of insulation members of the upsizing sleeve is formed from polyurethane, polysulfone, PEEK, ceramic, or epoxy.

18. An upsizing sleeve comprising:

a plurality of contact members, the plurality of contact members including outer surfaces, to form a first portion of an external surface of the upsizing sleeve, and at least one from the plurality of contact members including an inner surface housing a spring contact;

a plurality of relatively rigid insulation members, the plurality of insulation members comprising outer surfaces, to form a second portion of the external surface of the upsizing sleeve, and at least one from the plurality of insulation members including an inner surface housing a seal member; wherein the plurality of contact members is joined with the plurality of insulation members in an alternating fashion by means of mating interfaces.

19. The system of claim 18, wherein the inner surface of the at least one insulation member forms annular channel housing the seal member.

20. The system of claim 18, wherein the at least one insulation member further includes a side-wall surface forming a portion of an annular channel housing the spring contact.

21. The system of claim 18, wherein the inner surface of the at least one contact member forms an annular channel housing the spring contact.

22. The upsizing sleeve of claim 18, wherein the mating interfaces include adhesive.

23. The upsizing sleeve of claim 18, wherein the mating interfaces include flanges insertable within grooves.

24. The upsizing sleeve of claim 23, wherein the mating interfaces further include an adhesive.

25. The upsizing sleeve of claim 23, wherein the mating interfaces further include threaded surfaces.

26. The upsizing sleeve of claim 25, wherein the mating interfaces further include an adhesive.

27. The upsizing sleeve of claim 23, wherein the mating interfaces further include interlocking radial extensions.

28. The upsizing sleeve of claim 27, wherein the mating interfaces further include an adhesive.

29. The upsizing sleeve of claim 18, wherein the mating interfaces include a first surface overlapping on a second surface.

30. The upsizing sleeve of claim 29, wherein the mating interfaces further include an adhesive.

31. The upsizing sleeve of claim 29, wherein the mating interfaces further include threaded surfaces.

32. The upsizing sleeve of claim 31, wherein the mating interfaces further include an adhesive.

33. The upsizing sleeve of claim 29, wherein the mating interfaces further include interlocking radial extensions.

34. The upsizing sleeve of claim 33, wherein the mating interfaces further include an adhesive.

\* \* \* \* \*